(12) United States Patent
Clagg et al.

(10) Patent No.: US 11,325,912 B2
(45) Date of Patent: May 10, 2022

(54) REGIO-SELECTIVE SYNTHESIS OF IMIDAZO[1,2-A]PYRIMIDINES

(71) Applicant: Genentech, Inc., South San Francisco, CA (US)

(72) Inventors: Kyle Bradley Pascual Clagg, San Francisco, CA (US); Nicholas Andrew White, San Francisco, CA (US); Haiming Zhang, San Mateo, CA (US); Francis Gosselin, San Mateo, CA (US); William Nack, Glenview, IL (US); Paul D. O'Shea, Princeton, NJ (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/869,512

(22) Filed: May 7, 2020

(65) Prior Publication Data
US 2020/0369670 A1 Nov. 26, 2020

Related U.S. Application Data

(60) Provisional application No. 62/845,840, filed on May 9, 2019, provisional application No. 62/937,069, filed on Nov. 18, 2019.

(51) Int. Cl.
*C07D 487/04* (2006.01)
*C07F 9/24* (2006.01)

(52) U.S. Cl.
CPC .......... *C07D 487/04* (2013.01); *C07F 9/2454* (2013.01)

(58) Field of Classification Search
CPC .......................... C07D 487/04; C07F 9/2454
See application file for complete search history.

(56) References Cited

U.S. PATENT DOCUMENTS

2011/0182812 A1 7/2011 Szardenings et al.
2020/0354369 A1* 11/2020 Clagg .................. C07D 487/04

FOREIGN PATENT DOCUMENTS

WO 2015/173225 A1 11/2015

OTHER PUBLICATIONS

White, et al., Phosphoramidates as Steering Elements for Highly Selective Access to Complementary Imidazo[1,2-a]pyrimidine Isomers, Org. Lett., 21, 9527-9531 (2019). (Year: 2019).*

(Continued)

*Primary Examiner* — Erich A Leeser
(74) *Attorney, Agent, or Firm* — Genentech, Inc.; Richard G. A. Bone

(57) ABSTRACT

A method of regio-selectively synthesizing an imidazo-pyrimidine compound of formulae (XXa) or (XXb)

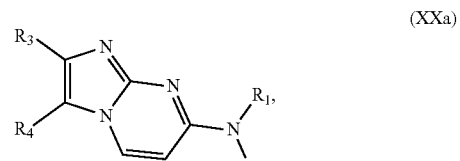

(XXa)

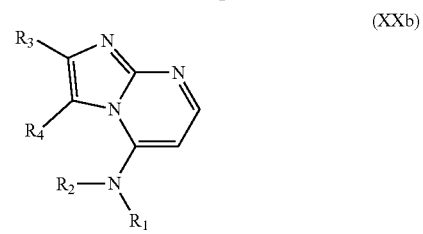

(XXb)

comprising a step of coupling a first compound of formula XX-P1a or XX-P1b with a second compound of formula XX-P2

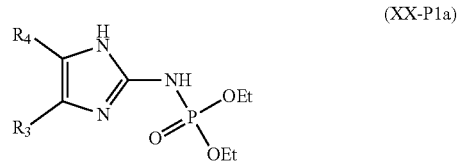

(XX-P1a)

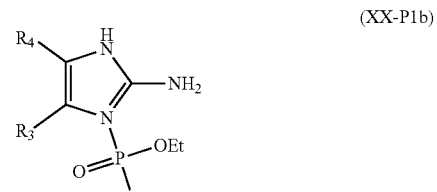

(XX-P1b)

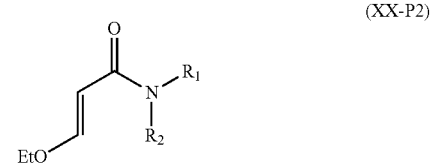

(XX-P2)

This annulation reaction between β-ethoxy acrylamides and phosphorylated aminoimidazoles to furnish imidazo[1,2-a]pyrimidin-amines relies on steering effects from endocyclic and exocyclic phosphorylated aminoimidazoles. The reaction furnishes either 2-amino or 4-amino constitutional isomers of imidazo[1,2-a]pyrimidines with good yields and ranges of 90:10-99:1 regio-selectivity. The reaction is useful in the synthesis of various tracer molecules used in the study of neurological conditions such as where $R_3$ and $R_4$ together with the imidazole ring atoms to which they are bonded form a phenyl ring and the products are substituted benzimidazopyrimidines. The reaction can be generalized to form imidazo[1,2-a]pyrimidines substituted at either of their 2- and 4-positions by alkoxy or thioalkyl groups.

8 Claims, 7 Drawing Sheets

(56) References Cited

OTHER PUBLICATIONS

Algual et al., "Comparative studies on conventional and microwave-assisted synthesis of a series of 2,4-di and 2,3,4-trisubstituted benzimidazo[1,2-a] pyrimidines and their antimicrobial activities" Cent. Eur. J. Chem. 7:337-342 ( 2009).

Bajwa and Sykes et al., "Synthesis and Structure of Some Azolo [a] pyrimidines, 2,6,7,8—Tetra hydro-1 H-cyclopenta[e]azolo[a]pyrimidines, 6,7-Dihydro-5H-cyclopenta [ f ]—azolo[a]pyrimidines, 7 ,8-Dihydro-G~-cyclopenta[f]-s-triazolo [4,3-b]pyridazine, 5,6,7,8-Tetrahydro-azolo [b]quinazolines, 6,7,8,9-Tetra hydroazolo[a]quinazolines, and 7,8,9,1 O-Tetrahydro-s-triazolo[3,4-a] phthalazine" J.C.S. Perkin I:3085-3094 ( 1979).

Bandyopadhyay et al., "Synthesis of some novel phosphorylated and thiophosphorylated benzimidazoles and benzothiazoles and their evaluation for larvicidal potential to Aedes albopictus and Culex quinquefasciatus" Bioorg. Med. Chem. Lett. 24:2934-2939 ( 2014).

El-Shorbagi et al., "An approach to hypertension crisis: Evaluation of new fused banzazoles; 2-ar-ylethenyl and 2,4-bis(arylethenyl) derivatives derived from 2,4-dimethylpyrimido [1,2-a] benzimidazole" Pharma Chemica 7:319-328 ( 2015).

Farghaly et al., "Synthesis, anti-HCV, antioxidant, and peroxynitrite inhibitory activity of fused benzosuberone derivatives" Eur. J. Med. Chem. 45:492-500 (2010).

Gao et al., "Concise and high-yiel synthesis of T808 and T808P for radiosynthesis of 18F-T808, a PET tau tracer for Alzheimer's disease" Bioorg Med Chem Lett 24(1):254-257 (Jan. 1, 2014).

Gobbi et al., "Identification of Three Novel Radiotracers for Imaging Aggregated Tau in Alzheimer's Disease with Positron Emission Tomography" J Med Chem 60:7350-7370 (Jun. 27, 2017).

International Search Report and Written Opinion for PCT/US2020/031953 dated Jul. 20, 2020.

Tseng et al., "A Simple regioselective synthesis of pyrimido[1,2a]benzimidazoles" J. Heterocycl. Chem 24:837-843 ( 1987).

White et al., "Phosphoramidates as Steering Elements for Highly Selective Access to Complementary Imidazo[1,2-a]pyrimidine Isomers" Org Lett 21(23):9527-9531 (Nov. 18, 2019).

Zhang et al., "A Highly Selective and Specific PET Tracer for Imaging of Tau Pathologies" Journal of Alzheimer's Disease 31(3):601-612 ( 2012).

* cited by examiner

REGIO-SELECTIVE SYNTHESIS OF IMIDAZO[1,2-A]PYRIMIDINES

CLAIM OF PRIORITY

This application claims benefit of priority under 35 U.S.C. § 119(e) to U.S. provisional application Ser. Nos. 62/845,840, filed May 9, 2019, and 62/937,069, filed Nov. 18, 2019, both of which are incorporated herein by reference in their entirety.

TECHNICAL FIELD

The technology described herein generally relates to organic synthesis, and more particularly relates to regio-selective synthetic pathways to molecules that contain substituted imidazo-pyrimidine groups.

BACKGROUND

The imidazo-pyrimidine moiety is a fused ring heterocyclic functional group that is frequently encountered in organic chemistry. It finds itself as a core member or part of a scaffold of so-called "small organic molecules" that are of interest in drug discovery and in therapeutic and diagnostic applications. In particular, the benzo[4,5]imidazo[1,2-a]pyrimidin-2-amine scaffold (a 3-fused ring system) has recently found utility in a number of positron emission tomography (PET) imaging agents that have strong binding affinity for tau protein plaques associated with neuropathologies such as Alzheimer's disease. (See, for example, Zhang, W.; Arteaga, J.; Cashion, D. K.; Chen, G.; Gangadharmath, U.; Gomez, L. F.; Kasi, D.; Lam, C.; Liang, Q.; Liu, C.; Mocharla, V. P.; Mu, F; Sinha, A.; Szardenings, A. K.; Wang, E.; Walsh, J. C.; Xia, C.; Yu, C; Zhao, T.; Kolb, H. C, "A highly selective and specific PET tracer for imaging of tau pathologies", J. Alzheimer's Dis. 2012, 31, 601-612; Gobbi, L. C.; Knust, H.; Körner, M; Honer, M.; Czech, C.; Belli, S.; Muri, D.; Edelmann, M. R.; Hartung, T.; Erbsmehl, I; Grall-Ulsemer, S.; Koblet, A.; Rueher, M.; Steiner, S.; Ravert, H. T.; Mathews, W. B.; Holt, D. P.; Kuwabara, H.; Valentine, H.; Dannals, R. F.; Wong, D. F.; Borroni, E, "Identification of three novel radiotracers for imaging aggregated tau in Alzheimer's disease with positron emission tomography." J. Med. Chem., 2017, 60, 7350-7370; Gao, M.; Wang, M.; Zheng, Q-. H. "Concise and high-yield synthesis of T-808 and T808P for radiosynthesis of [$^{18}$F]-T808, a PET tau tracer for Alzheimer's disease", Bioorg. Med. Chem. Lett., 2014, 24, 254-257.) This scaffold is also found in investigational tau degrader molecules (see, for example, Crew, A. P.; Berlin, M.; Flanagain, J. J.; Dong, H.; Ishchenko, A, "Tau-protein targeting protacs and associated methods of use", U.S. Patent App. Pub. 20180125821 A1, May 10, 2018) and in imaging agents for identification of other proteins associated with neurodegenerative conditions such as Huntington's disease (see, for example, Dominguez, C.; Wityak, J.; Bard, J.; Kiselyov, A.; Brown, C. J.; Prime, M. E.; Johnson, P. D.; Clark-Frew, D.; Schaertl, S.; Herrmann, F.; Grimm, S, K; Kahmann, J. D.; Scheich, C, "Probes for Imaging Huntington Protein", PCT Pub. 2016033440 A1, Mar. 3, 2016). More generally, the benzo[4,5]imidazo [1,2-a]pyrimidine motif has been incorporated into molecules which have shown anti-neurodegenerative (see, for example, Pavlov, P. Winblad, B. Pyrimidobenzimidazoles for use in the treatment and prevention of neurodegenerative disorders. PCT Pub. 2017168137 A1 Oct. 5, 2017), anti-hypertensive (see, for example, El-Shorbagi, A-N. A.; Husein, M. A. An approach to hypertension crisis: Evaluation of new fused banzazoles; 2-ar-ylethenyl and 2,4-bis (arylethenyl) derivatives derived from 2,4-dimethylpyrimido [1,2-a] benzimidazole. Pharma Chemica 2015, 7, 319-328), anti-microbial (see, for example, Algul, O.; Meric, A.; Polat, S.; Yuskek, N. D.; Serin, M. S. Comparative studies on conventional and microwave-assisted synthesis of a series of 2,4-di and 2,3,4-trisubstituted benzimidazo[1,2-a] pyrimidines and their antimicrobial activities. Cent. Eur. J. Chem. 2009, 7, 337-342), and antiviral activity (see, for example, Farghaly, T. A.; Hafez, N. A. A.; Ragab, E. A.; Awad, H. M.; Abdalla, M. M. Synthesis, anti-HCV, antioxidant, and per-oxynitrite inhibitory activity of fusedbenzosuberone derivatives. Eur. J. Med. Chem. 2010, 45, 492-500).

For clinical applications of biomarker molecules, a radioisotope, such as $^{18}$F, is introduced into a precursor molecule immediately prior to administration of the compound to a patient. Correspondingly, an efficient synthesis of the precursor is particularly desirable because the precursor must be available in large quantities that are ready for labeling.

Traditionally, benzo[4,5]imidazo[1,2-a]pyrimidine derivatives have been synthesized via the condensation of aminoimidazoles with enones or enals bearing a leaving group in the β-position. (See, for example, Bajwa, J. S.; Sykes, P. J. Synthesis and Structure of Some Azolo [a] pyrimidines, 2,6,7,8-tetrahydro-1H-cyclopenta[e]azolo[a] pyrimidines, 6,7-dihydro-5H-cyclopenta[f]-azolo[a]pyrimidines, 7,8-dihydro-6H-cyclopenta[f]-s-triazolo[4,3-b] pyridazine, 5,6,7,8-tetrahydro-azolo [blquinazolines, 6,7,8, 9-Tetra hydroazolo[a]quinazolines, and 7,8,9,10-Tetrahydro-s-triazolo[3,4-a] phthalazine. J. Chem. Soc. Perkin Trans. 1 1979, 12, 3085-3094; and Tseng, S. S.; Epstein, J. W.; Brabander, H. J.; Francisco, G, "A simple regioselective synthesis of pyrimido[1,2-a]benzimidazoles", J. Heterocycl. Chem., 1987, 24, 837-843.) This approach generally provides imidazopyrimidine products in high yield and with good isomeric selectivity. However, the scope of this approach is limited to α,β-unsaturated aldehydes and ketones, meaning that the products are limited to unsubstituted or alkylated imidazopyrimidines. Therefore there is a need for a scheme that provides direct access to other functionalized imidazo[1,2-a]pyrimidin-amines from aminoimidazoles.

The discussion of the background herein is included to explain the context of the technology. This is not to be taken as an admission that any of the material referred to was published, known, or part of the common general knowledge as at the priority date of any of the claims found appended hereto.

Throughout the description and claims of the instant application the word "comprise" and variations thereof, such as "comprising" and "comprises", is not intended to exclude other additives, components, integers or steps.

SUMMARY

The instant disclosure addresses the regio-selective synthesis of heterocyclic organic molecules, specifically those that contain an imidazo-pyrimidine moiety. In particular, the disclosure comprises a coupling step that can make a substituted imidazo-pyrimidine in high yield.

In particular, the present disclosure includes a process for synthesizing substituted imidazo-pyrimidines of formulae (XXa) and (XXb).

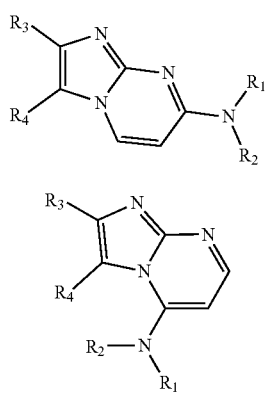

wherein the method comprises:
coupling a first amino-imidazole compound of formula XX-P1a or XX-P1b with a second acrylamide compound of formula XX-P2

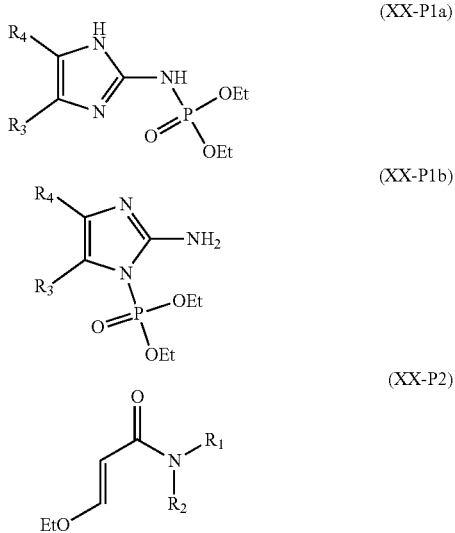

It is understood by one skilled in the art that the following structures are tautomers of each other:

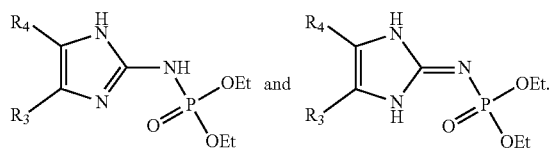

It has been observed that the right-hand structure is found in the solid state, whereas in solution the two structures are in tautomeric equilibrium. In the description herein, the two tautomers may be used interchangeably, unless from context a particular tautomer is intended.

In formula XX-P2, $R_1$ and $R_2$ are each independently selected from alkyl, alkenyl, alkynyl, carbocyclyl, aryl or heteroaryl, wherein any such group may optionally be substituted independently at one or more of its available positions by a group selected from: hydroxyl, amino, alkoxy, aminoalkyl, carboxy, cyano, thio, halo, aryl and heteroaryl, or $R_1$ and $R_2$ together form a cycloalkyl ring having 3-12 atoms, and wherein the cycloalkyl ring is optionally and independently substituted in any one or more of its available positions by a group selected from hydroxyl, amino, alkoxy, aminoalkyl, carboxy, cyano, thio, halo, aryl and heteroaryl.

In formulae XX-P1a and XX-P1b, $R_3$ and $R_4$ are each independently selected from alkyl, alkenyl, alkynyl, carbocyclyl, aryl or heteroaryl, wherein any such group may optionally be substituted independently at one or more of its available positions by a group selected from: hydroxyl, amino, alkoxy, aminoalkyl, thio, cyano, halo, aryl, and heteroaryl.

In other embodiments, $R_3$ and $R_4$ together form a phenyl ring, wherein the phenyl ring is optionally and independently substituted in any one or more of its 4 available positions by a group selected from hydroxyl, amino, alkoxy, aminoalkyl, thio, nitro, sulfonyl, carboxy, cyano, halo, aryl, and heteroaryl, wherein any such group may optionally be substituted independently at one or more of its available positions by a group selected from: hydroxyl, amino, alkoxy, aminoalkyl, thio, cyano, halo, aryl or heteroaryl.

In preferred embodiments, the coupling between XX-P1a or XX-P1b and XX-P2 takes place in the presence of $POCl_3$, $ET_3N$, and a non-aqueous solvent.

DETAILED DESCRIPTION

Figure 1:
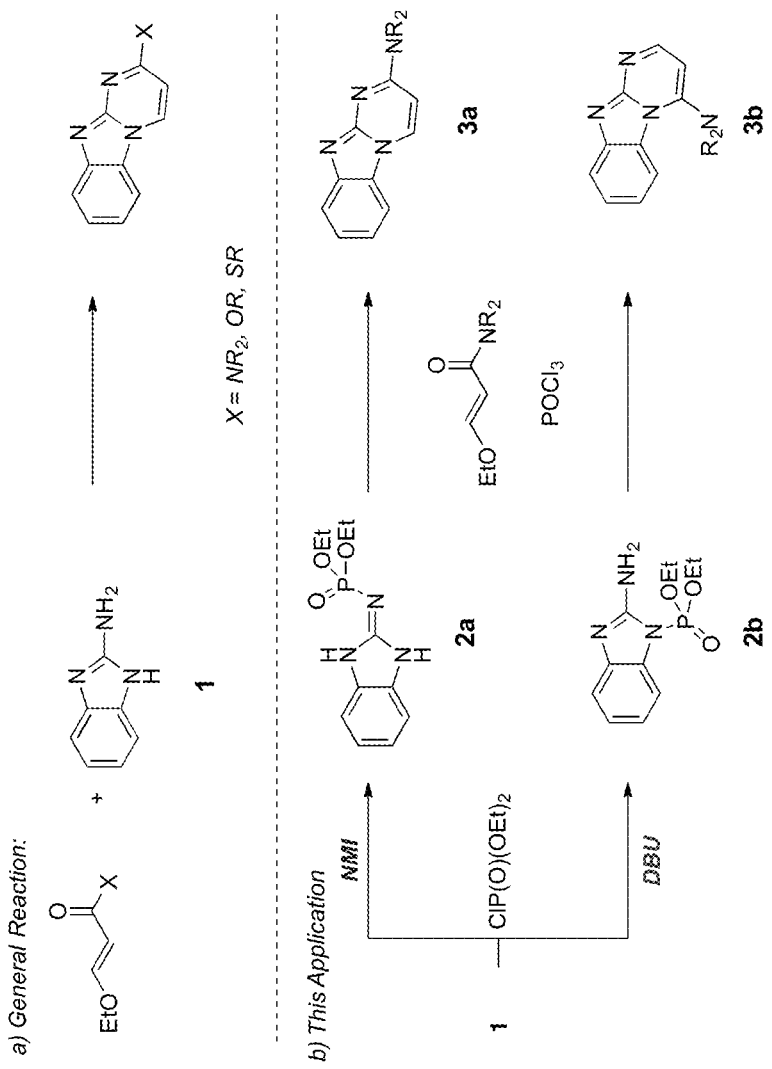
FIG. 1 shows synthetic approaches to benzo[4,5]imidazo[1,2-a]pyrimidine scaffolds from benzimidazole precursors, process as further described herein.

Reference will now be made in detail to certain embodiments of the synthetic process, examples of which are illustrated in the accompanying structures and formulas. While the process will be described in conjunction with the enumerated embodiments, it will be understood that they are not intended to limit the invention to those embodiments. On the contrary, the description is intended to cover all alternatives, modifications, and equivalents which may be included within the scope of the present process as defined by the claims. One skilled in the art will recognize many methods and materials similar or equivalent to those described herein, which could be used in the practice of the present process, so that the present process is not limited to the methods and materials described. In the event that one or more of the cited literature, patents, and similar materials differs from or contradicts the description herein, including but not limited to defined terms, term usage, described techniques, or the like, this description controls. Unless otherwise defined, all technical and scientific terms used herein have the same meaning as commonly understood by one of ordinary skill in the art to which this process belongs. Although methods and materials similar or equivalent to those described herein can be used in the practice or testing of the process, suitable methods and materials are described below. The nomenclature used in this application is based on the *ACS Style Guide* and the *The Journal of Organic Chemistry* list of "Standard Abbreviations and Acronyms" (both published by the American Chemical Society, Washington, D.C.), as well as on IUPAC systematic nomenclature, unless indicated otherwise.

Definitions

Chemical elements are identified in accordance with the Periodic Table of the Elements, CAS version, Handbook of Chemistry and Physics, 75th Ed.

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus, or silicon, and the quaternized form of any nitrogen).

The term "saturated" means a functional group in which all bonds between non-hydrogen atoms are single covalent bonds.

The term "unsaturated", as used herein, means that a functional group has one or more pairs of non-hydrogen atoms linked by a double or triple bond. A pair of non-hydrogen atoms bonded to one another by a double or triple bond can be referred to as a unit of unsaturation. A functional group that contains two or more units of unsaturation separated from one another by a single bond is often referred to as conjugated.

As used herein, the term "partially unsaturated" refers to a ring moiety that includes at least one double or triple bond between ring atoms but the ring moiety is not aromatic.

An aromatic ring or ring system (comprising one or more rings sharing a pair of atoms as an edge) is a ring that is fully conjugated. Typically an aromatic ring is characterized by the so-called Hückel rule in which the number of conjugated pi-electrons obeys the formula 4n+2, where n is an integer.

The term "alkyl," as used herein, refers to a saturated linear or branched-chain monovalent hydrocarbon radical. In one embodiment, the alkyl radical is one to eighteen carbon atoms ($C_1$-$C_{18}$). In other embodiments, the alkyl radical is $C_1$-$C_{16}$, $C_1$-$C_{15}$, $C_1$-$C_{13}$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include but are not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2 pentyl (—CH($CH_3$)$CH_2CH_2CH_3$), 3-pentyl (—CH($CH_2CH_3$)$_2$), 2-methyl-2-butyl (C($CH_3$)$_2CH_2CH_3$), 3-methyl-2-butyl (—CH($CH_3$)CH($CH_3$)$_2$), 3-methyl-1-butyl ($CH_2CH_2CH(CH_3)_2$), 2-methyl-1-butyl (—$CH_2CH(CH_3)CH_2CH_3$), 1-hexyl ($CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2CH(CH_3)_2$), 3,3-dimethyl-2-butyl (—CH($CH_3$)C($CH_3$)$_3$, heptyl, octyl, nonyl, decyl, undecyl, and dodecyl.

The term "alkenyl," as used herein, denotes a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical comprises two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH═$CH_2$), prop-1-enyl (—CH═$CHCH_3$), prop-2-enyl (—$CH_2$CH═$CH_2$), 2 methylprop-1-enyl, but-1-enyl, but-2-enyl, but-3-enyl, buta-1,3-dienyl, 2 methylbuta-1,3-diene, hex-1-enyl, hex-2-enyl, hex-3-enyl, hex-4-enyl and hexa-1,3-dienyl.

The term "alkynyl," as used herein, refers to a linear or branched monovalent hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Further examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but 3-ynyl.

The term "haloalkyl," as used herein, refers to an alkyl as defined herein that is substituted with one or more (e.g., 1, 2, 3, or 4) halo groups.

The term "carbocyclyl" used alone or as part of a larger moiety, refers to a saturated, partially unsaturated, or aromatic ring system having 3 to 20 carbon atoms. In one embodiment, carbocyclyl includes ring systems having 3 to 12 carbon atoms ($C_3$-$C_{12}$). In another embodiment, carbocyclyl includes ring systems having $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicyclic ring system, includes $C_7$-$C_{12}$. In another embodiment, carbocyclyl, as a spiro system, includes $C_5$-$C_{12}$. Examples of monocyclic carbocyclyls include but are not limited to cycloalkyl rings such as: cyclopropyl, cyclobutyl, cyclopentyl, 1 cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl. Examples of bicyclic carbocyclyls having 7 to 12 ring atoms include [4,3], [4,4], [4,5], [5,5], [5,6] or [6,6] ring systems, for example bicyclo[2.2.1]heptanyl, bicyclo[2.2.2]octanyl, naphthalenyl, and bicyclo[3.2.2]nonanyl. Examples of spiro-carbocyclyls include spiro[2.2]pentanyl, spiro[2.3]hexanyl, spiro[2.4]heptanyl, spiro[2.5]octanyl and spiro[4.5]decanyl. The term carbocyclyl includes aryl (but not heteroaryl) ring systems as defined elsewhere herein.

An alicyclic ring is a carbocyclic ring that is not an aryl or aromatic ring.

The term "alkoxy" refers to a linear or branched monovalent radical represented by the formula —OR in which R is alkyl. Alkoxy groups include but are not limited to methoxy, ethoxy, propoxy, and isopropoxy.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment, aryl includes an aryl ring fused to one or more carbocyclic rings, such as indanyl, phthalimidyl, naphthimidyl, phenantridinyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In another embodiment, heteroaryl includes bicyclic or tricyclic aromatic groups where one or more ring atoms (e.g., 1, 2, 3, 4, 5, 6, 7, or 8) is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-onyl. A heteroaryl group may be mono-, bi- or tri cyclic.

As used herein, the term "heterocyclyl" refers to a "carbocyclyl" as defined herein, wherein one or more (e.g., 1, 2, 3, or 4) carbon atoms have been replaced with a heteroatom (e.g., O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein. In one embodiment, heterocyclyl includes 5-6 membered monocyclic cyclic groups where one or more ring atoms is nitrogen, sulfur or oxygen (e.g., 1, 2, 3 or 4) that is independently optionally substituted. In another embodiment, heterocyclyl includes bicyclic or tricyclic groups where one or more ring atoms (e.g., 1, 2, 3, 4, 5, 6, 7, or 8) is nitrogen, sulfur or oxygen that is independently optionally substituted.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5 6 membered monocycles. In one example, the heterocyclyl group includes 0 to 3 double bonds. Any nitrogen or sulfur heteroatom may optionally be oxidized (e.g., NO, SO, SO2), and any nitrogen heteroatom may optionally be quaternized (e.g., $[NR_4]+$ Cl—, $[NR_4]+OH$—). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6 azabicyclo[3.1.1]heptanyl, 3-azabicyclo[3.1.1]heptanyl, 3 azabicyclo[4.1.0]heptanyl, azabicyclo[2.2.2]hexanyl, 2 azabicyclo[3.2.1]octanyl, 8-azabicyclo[3.2.1]octanyl, 2 azabicyclo[2.2.2]octanyl, 8-azabicyclo[2.2.2]octanyl, 7 oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, and 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5 membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, structures depicted herein are also meant to include compounds that differ only in the presence of one or more isotopically enriched atoms in addition to any isotopically enriched atom that has been explicitly identified. For example, compounds, wherein the independent replacement or enrichment of one or more hydrogen by deuterium or tritium, carbon by $^{13}C$- or $^{14}C$ carbon, nitrogen by a $^{15}N$ nitrogen, sulfur by a $^{33}S$, $^{34}S$ or $^{36}S$ sulfur, or oxygen by a $^{17}O$ or $^{18}O$ oxygen are included. Such compounds are useful, for example, as analytical tools, as probes in biological assays, or as therapeutic agents.

The term "deuterated" means that a hydrogen atom is replaced by a deuterium atom at a level above its natural abundance at one or more positions of a molecule. When a particular position is deuterated, it is understood that the abundance of deuterium at that position is substantially greater than the natural abundance of deuterium, which is 0.015%. A deuterated position typically has a minimum isotopic enrichment factor of at least 3,000 (45% deuterium incorporation). The term "isotopic enrichment factor" as used herein means the ratio between the isotopic abundance and the natural abundance of a specified isotope.

As between chemical names and structures shown, if there are any discrepancies, the structure prevails.

As used herein, "a" or "an" means one or more, unless clearly indicated otherwise.

Overview of Synthetic Methods

In general, the methods disclosed provide efficient synthetic routes to compounds of formula Xa and Xb, wherein X is —$OR_1$, —$SR_1$, or —$NR_1R_2$, wherein $R_1$ and $R_2$ are defined elsewhere herein.

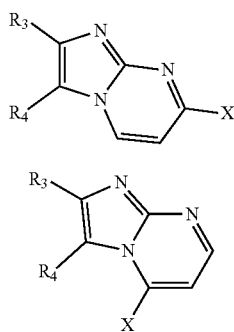

As described by way of specific synthetic schemes in the Examples that follow, the invention further comprises a method of synthesizing compounds of formula (XXa) and (XXb):

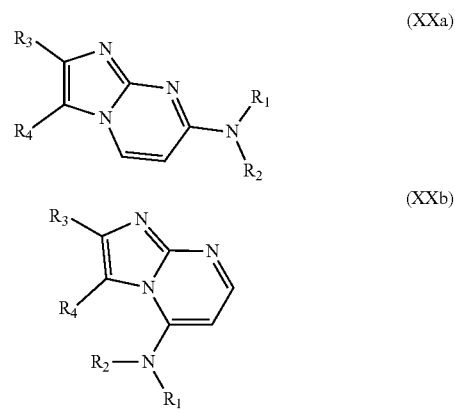

In preferred embodiments, selective N-phosphorylation of amino-imidazoles results in a key steering element that controls isomeric selectivity in the condensation of β-ethoxy acrylamides and aminoimidazoles to furnish imidazo[1,2-a]pyrimidines, and in preferred embodiments benzo-imidazo[1,2-a]pyrimidines from benzo-aminoimidazoles. Conditions that provide highly selective (such as 99:1) phosphorylation at the endo- or exo-cyclic nitrogen of imidazole derivatives are also described.

For example, differentially N-phosphorylated coupling partners 2a and 2b provide access to either benzo[4,5]imidazo[1,2-a]pyrimidin-2-amine (3a) or benzo[4,5]imidazo[1,2-a]pyrimidin-4-amine (3b) isomers, respectively, with a high degree of selectivity (FIG. 1). Either the 2-amino or 4-amino isomer of the imidazo[1,2-a]pyrimidine products can be isolated in yields ranging from 64-95%. Mass spectrometric and computational analysis can give insight into the mechanism of this selective transformation.

Synthesis of amino-imidazo-pyrimidines

It is an aspect of the processes described herein that a method of synthesizing amino-imidazo-pyrimidines of formula (XXa) and (XXb) is provided.

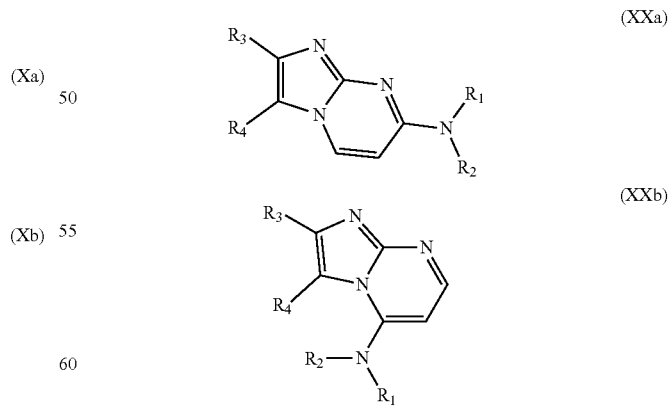

A method of synthesizing an imidazo-pyrimidine compound of formula (XXa) or (XXb) comprises coupling a first compound of formula XX-P1a or XX-P1b with a second compound of formula XX-P2

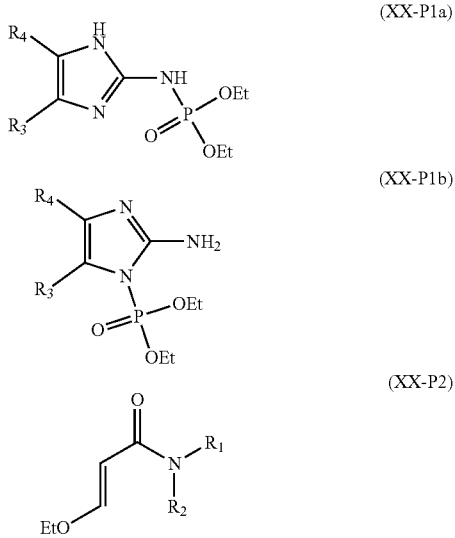

wherein:

In formula XX-P2, (as well as XXa, XXb, Xa and Xb herein) $R_1$ and $R_2$ are each independently selected from alkyl, alkenyl, alkynyl, carbocyclyl, aryl or heteroaryl, wherein any such group may optionally be substituted independently at one or more of its available positions by a group selected from: hydroxyl, amino, alkoxy, aminoalkyl, thio, carboxy, cyano, halo, alkyl, cycloalky, aryl and heteroaryl. In another embodiment, $R_1$ and $R_2$ together with the nitrogen to which they are bonded form a ring having 3-12 atoms, wherein the ring is optionally and independently substituted in any one or more of its available positions by a group selected from hydroxyl, amino, alkoxy, aminoalkyl, carboxy, cyano, thio, halo, alkyl, haloalkyl, cycloalkyl, aryl, and heteroaryl. If the ring comprising $R_1$ and $R_2$ is substituted by a group that admits of further substitution such as alkyl, cycloalkyl, aryl or heteroaryl, then that group can also be substituted by a further group or groups selected from: amino, alkoxy, aminoalkyl, carboxy, cyano, thio, halo, alkyl, haloalkyl, cycloalkyl, nitro, or sulfonyl.

In formula XX-P1a and XX-P1b, $R_3$ and $R_4$ are each independently selected from alkyl, alkenyl, alkynyl, haloalkyl, carboxylate, carbocyclyl, aryl or heteroaryl, wherein any such group may optionally be substituted independently at one or more of its available positions by a group selected from: hydroxyl, amino, alkoxy, aminoalkyl, thio, cyano, halo, aryl and heteroaryl. In other embodiments, $R_3$ and $R_4$ together with the two carbon atoms of the imidazole ring to which they are respectively bonded form a phenyl ring, wherein the phenyl ring is optionally and independently substituted in any one or more of its 4 available positions by a group selected from hydroxyl, amino, alkoxy, aminoalkyl, thio, nitro, sulfonyl, carboxy, cyano, halo, alkyl, cycloalkyl, aryl, and heteroaryl, wherein any such group may optionally be further substituted independently at one or more of its available positions by a group selected from: hydroxyl, amino, alkoxy, aminoalkyl, thio, nitro, haloalkyl, sulfonyl, cyano, halo, alkyl, cycloalkyl, aryl or heteroaryl.

In one embodiment, a compound of formula XX-P1a can be formed by reacting 2-amino-imidazole with phosphorylating agent such as $(EtO)_2P(=O)Cl$. In general, a suitable phosphorylating agent is $(RO)_2P(=O)Cl$, wherein R is an alkyl, cycloalkyl, aryl, or halogenated variants thereof. For example, R can be methyl, trifluoromethyl, phenyl, propyl, or butyl.

In some embodiments, the phosphorylating agent, such as $PCl(O)(OEt)_2$ is formed in situ by reacting an alkyl hydrogen phosphate such as diethyl hydrogen phosphate with a chlorinating agent such as 1,3,5-trichloro-1,3,5-triazinane-2,4,6-trione.

In one embodiment, a compound of formula XX-P2 can be formed in two steps: first by reacting (E)-3-ethoxy-acrylic acid with a chlorinating agent such as sulfonyl chloride $(SOCl_2)$; second, followed by reacting (E)-3-ethoxyacryloyl chloride with an amine, $R_1R_2NH$ (with $R_1$ and $R_2$ as defined elsewhere herein) in an aprotic solvent. In such embodiments, other suitable chlorinating agents include oxalyl chloride $(COCl)_2$ and alkyl chloroformates such as methyl, ethyl, isopropyl, isobutyl chloroformate. In other embodiments, ways to form the amide bond in XX-P2 are by using amide coupling reagents such as CDI (carbonyl diimidazole), EDC (1-ethyl-3-(3-dimethylaminopropyl)carbodiimide), and HATU (hexafluorophosphate azabenzotriazole tetramethyl uronium).

In preferred embodiments, the coupling between XX-P1a or XX-P1b and XX-P2 takes place in the presence of $POCl_3$ or $PCl_5$, $Et_3N$, and a non-aqueous solvent such as MeTHF, MeCN or mixtures thereof. The $POCl_3$ (or $PCl_5$) achieves activation of the acrylamide compound (by converting the $C(=O)N$ to $C(Cl)=N^+$). Other agents such as $SOCl_2$ may also achieve this. It may be necessary to heat the reaction mixture, such as to 60-100° C., for example 80° C. $Et_3N$ acts as a base that mops up acids that are generated as side products during the reaction. Its role can be played by other bases such as $^nBu_3N$, $iPr_2NEt$, and N-methylmorpholine."

EXAMPLES

General Information

All new compounds were characterized by $^1H$ NMR, $^{13}C$ NMR, IR, melting point, and HRMS.

$^1H$, $^{13}C$, $^{19}F$, and $^{31}P$ nuclear magnetic resonance spectra were recorded on a Bruker 400 MHz instrument at room temperature.

All $^1H$ NMR spectra were measured in parts per million (ppm) relative to residual chloroform signal (δ 7.26), methanol (δ 3.31), DMSO (δ 2.50) or acetic acid (δ 2.04) in the deuterated solvent unless otherwise stated. Data for $^1H$ NMR are reported as follows: chemical shift, multiplicity (br=broad signal, s=singlet, d=doublet, t=triplet, q=quartet, p=pentet, m=multiplet), coupling constants in Hertz and integration.

All $^{13}C$ NMR spectra are reported in ppm relative to deuteronchloroform (δ 77.06) methanol-$d_4$ (δ 49.00), DMSO-$d_6$ (δ 39.53), or acetic acid-$d_4$ (δ 20.0) and were obtained with complete $^1H$ decoupling unless otherwise stated.

All $^{19}F$ NMR spectra were obtained with complete $^1H$ decoupling.

All $^{31}P$ NMR spectra were obtained with complete $^1H$ decoupling.

HPLC analyses were performed on an Agilent 1260 Infinity HPLC system with a UV detector at 254 nm using an Ace Super C18 column.

Melting points were obtained using a Buchi B-540 Melting Point Apparatus and are uncorrected.

IR spectra were recorded on a Bruker Alpha Platinum-neat spectrometer and are reported in frequency of absorption (cm$^{-1}$).

High resolution mass spectrometry (HRMS) data were acquired on a Thermo Scientific Orbitrap Fusion mass spectrometer.

All reagents and solvents were purchased from commercial suppliers and used with no additional purification. Anhydrous solvent (acetonitrile and 2-methyltetrahydrofuran) was utilized, but no effort was undertaken to further increase the purity of other commercially available solvents. All reactions were carried out in screw-cap vials equipped with Teflon septa under a nitrogen atmosphere. Yields reported are of isolated material.

Flash column chromatography was performed using a Teledyne Isco CombiFlash® Rf instrument with pre-packed RediSepRf Gold silica cartridges.

Example 1: Synthesis of 2-(1-(benzo[4,5]imidazo[1,2-a]pyridin-3-yl)piperidin-4-yl)ethyl-1,1,2,2-d4 4-methylbenzenesulfonate Example 1 describes a representative synthesis of a molecule using a step of conjugating an acrylamide with a phosphorylated imidazole.

Step 1—Formation of Diethyl (1H-benzo[d]imidazol-2-yl)phosphoramidate

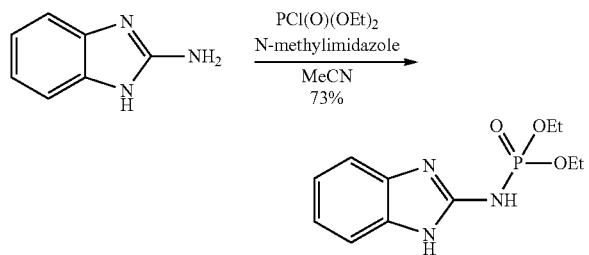

To a reactor under nitrogen was charged 1H-benzo[d]imidazol-2-amine (0.7882 kg, 6.002 mol, 1.00 equiv) followed by MeCN (5.333 L). To this mixture was then added N-methylimidazole (0.6693 kg, 8.103 mol, 1.35 equiv) followed by MeCN (0.460 L) to rinse the reaction vessel. This slurry was then stirred at 20° C. for a minimum of 15 min. Next, PCl(O)(OEt)$_2$ (1.4070 kg, 8.154 mol, 1.35 equiv.) was added dropwise over 1 h keeping the internal temperature below 30° C. Upon completion of the PCl(O)(OEt)$_2$ addition, MeCN (0.455 L) was added to rinse the reaction vessel. This slurry was then stirred at 20° C. for a minimum of 12 h. Upon completion of reaction, the vessel was cooled to 0° C. over a minimum of 30 min and then stirred at this temperature for a minimum of 2 h. This mixture was then filtered and the wetcake was washed with two portions of MeCN (3.2 L). The solids were dried under vacuum at 40° C. for a minimum of 12 h to afford diethyl (1H-benzo[d]imidazol-2-yl)phosphoramidate as an off-white solid (1.2144 kg, corrected yield: 73%, 99.5% HPLC purity): mp 229° C.

$^1$H NMR (400 MHz, Methanol-d$_4$) δ 7.20 (dt, J=7.6, 3.8 Hz, 2H), 7.11 (dd, J=5.9, 3.2 Hz, 2H), 4.07 (p, J=7.2 Hz, 4H), 1.32 (t, J=7.1 Hz, 6H); $^{13}$C NMR (101 MHz, Methanol-d$_4$) δ 123.4, 111.2, 63.4, 63.4, 16.6, 16.6; $^{31}$P NMR (162 MHz, Methanol-d4) δ 7.31.

Step 2—2-(1-(benzo[4,5]imidazo[1,2-a]pyrimidin-2-yl)piperidin-4-yl)ethyl-1,1-d$_2$ benzoate

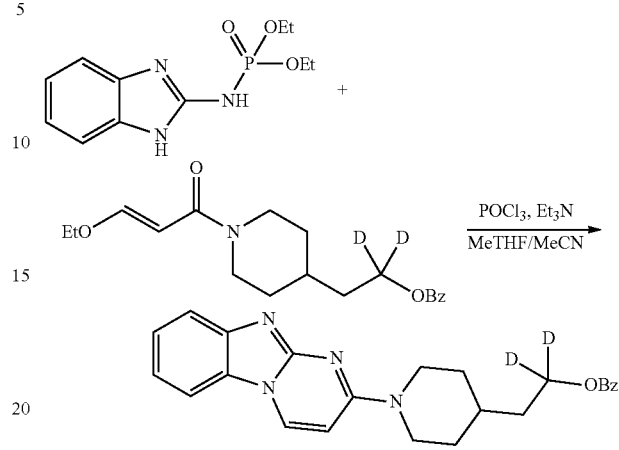

To a reactor under nitrogen was charged MeCN (5.00 L) followed by (E)-2-(1-(3-ethoxyacryloyl)piperidin-4-yl) ethyl-1,1-d$_2$ benzoate (1.00 kg, 3.00 mol, 1.0 equiv) and diethyl (1H-benzo[d]imidazol-2-yl)phosphoramidate (888.5 g, 3.30 mol, 1.1 equiv). (The benzoate compound can be synthesized by methods known in the art, or as described in Example 2, or in the application to which the instant application claims benefit of priority.) MeTHF (5.00 L) was charged followed by Et$_3$N (152.0 g, 1.50 mol, 0.5 equiv). Next, the reactor was cooled between −10-10° C. and POCl$_3$ (1.01 kg, 6.60 mol, 2.2 equiv) was added over a minimum 30 min while maintaining the internal temperature between −10 and 10° C. Upon completion of the addition, the contents were then heated to 65-95° C. ° C. over a minimum of 2 h and the reaction held at an internal temperature of 80° C. for a minimum of 1.5 h. After completion of reaction was confirmed, the reactor was cooled to 15-25° C. then added to a 25 w/w % solution of K$_2$CO$_3$ (premade by mixing water (5.0 L) with K$_2$CO$_3$ (1.67 kg) and stirring at 20° C. for a minimum of 15 min.) over a minimum of 15 min. while keeping the internal temperature below 30° C. This was then stirred for a minimum of 15 min. after which the layers were separated and the aqueous drained to waste.

Example 2: Synthesis of 2-(1-(benzo[4,5]imidazo[1,2-a]pyridin-3-yl)piperidin-4-yl)ethyl-1,1,2,2-d4 4-methylbenzenesulfonate Step 1—Preparation of diethyl (1H-benzo[d]imidazol-2-yl)phosphoramidate

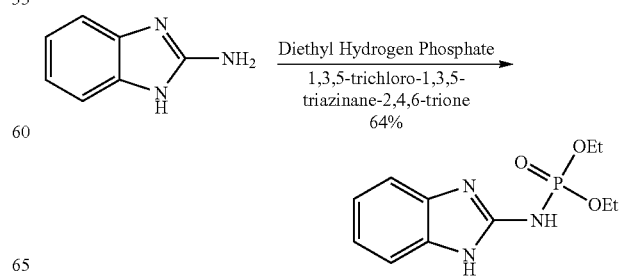

To a flask at 15-25° C. under nitrogen was charged 1,3,5-trichloro-1,3,5-triazinane-2,4,6-trione (5.55 g, 23.8 mmol, 0.31 equiv) and MeCN (35.0 mL). The mixture was stirred until homogenous. Diethyl hydrogen phosphate (10.3 g, 75.1 mmol, 9.69 mL, 1.00 eq) and Et$_3$N (15.2 g, 150.2 mmol, 20.9 mL, 2.00 eq) were then added and the flask was heated to 85° C. and stirred for 30 min, at which point precipitation had occurred. The jacket was then cooled to 0° C. and 1H-benzo[d]imidazol-2-amine (10.0 g, 75.1 mmol, 1.00 equiv), dissolved in THF (35.0 mL), was charged to the flask. The reaction mixture was then warmed to 15-25° C. and stirred for 1 h. Upon confirmation of reaction completion, the reaction was quenched with water (100.0 mL) then extracted with two portions of ethyl acetate (200.0 mL). The combined organic layers were dried over Na$_2$SO$_4$, filtered, and then concentrated under reduced pressure to afford compound diethyl (1H-benzo[d]imidazol-2-yl)phosphoramidate as a brown solid (13.0 g, 48.2 mmol, 64% yield).

$^1$H NMR (400 MHz, CDCl$_3$) δ ppm 7.34 (dd, J=18.03, 7.89 Hz, 2H), 7.19 (td, J=7.67, 1.04 Hz, 1H), 7.05 (td, J=7.70, 0.98 Hz, 1H), 6.13-6.74 (m, 2H), 4.20-4.34 (m, 2H), 4.00-4.19 (m, 3H), 1.33 (td, J=7.09, 0.86 Hz, 6H).

Step 2—Preparation of (E)-3-ethoxyacryloyl Chloride

To a solution of (E)-3-ethoxyacrylic acid (4.40 g, 37.8 mmol, 1.00 equiv) in DCM (20.0 mL) was added SOCl$_2$ (4.51 g, 37.8 mmol, 2.75 mL, 1.00 equiv) at 25° C. The mixture was stirred at 40° C. for 1 h. After reaction completion was confirmed, the mixture was evaporated to dryness to afford (E)-3-ethoxyacryloyl chloride as a yellow oil (5.10 g, 37.9 mmol, 100% yield). This was used directly in the next step without purification.

Step 3—(E)-2-(1-(3-ethoxyacryloyl)piperidin-4-yl) ethyl-1,1,2,2-d$_4$ Benzoate

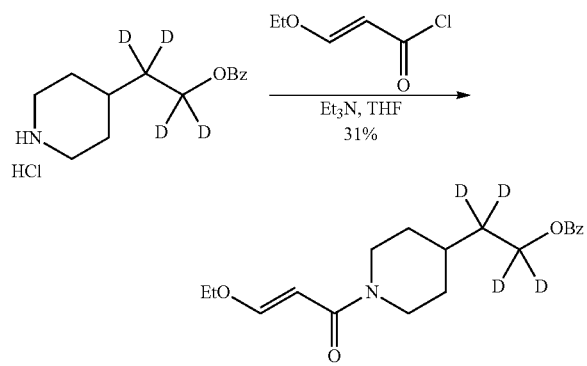

To a solution of 2-(piperidin-4-yl)ethyl-1,1,2,2-d$_4$ benzoate hydrochloride (8.52 g, 31.1 mmol, 1.00 equiv) and Et$_3$N (3.15 g, 31.1 mmol, 4.33 mL, 1.00 equiv) in THF (15.0 mL) at 0-10° C. was added the crude (E)-3-ethoxyacryloyl chloride (5.02 g, 37.3 mmol, 1.2 equiv). The reaction was stirred at 0-10° C. for 1 h. Upon confirmation of reaction completion, H$_2$O (50.0 mL) was added and resulting aqueous was extracted with three portions of EtOAc (50.0 mL). The organic phases were then combined, dried over Na$_2$SO$_4$, and evaporated to dryness. The residue was then slurried in MTBE (10.0 mL) then filtered to afford (E)-2-(1-(3-ethoxyacryloyl)piperidin-4-yl)ethyl-1,1,2,2-d$_4$ benzoate (3.20 g, 9.54 mmol, 31% yield) as a yellow solid.

$^1$H NMR (400 MHz, DMSO-d$_6$) δ ppm 8.03 (br d, J=7.34 Hz, 2H), 7.67-7.78 (m, 1H), 7.51-7.65 (m, 2H), 7.44 (d, J=11.86 Hz, 1H), 5.91 (d, J=11.86 Hz, 1H), 4.09-4.60 (m, 2H), 3.93-4.03 (m, 2H), 2.66-3.12 (m, 2H), 1.61-1.89 (m, 3H), 1.29 (t, J=7.03 Hz, 3H), 1.00-1.18 (m, 2H).

Step 4—2-(1-(benzo[4,5]imidazo[1,2-a]pyrimidin-2-yl)piperidin-4-yl)ethyl-1,1,2,2-d$_4$ Benzoate

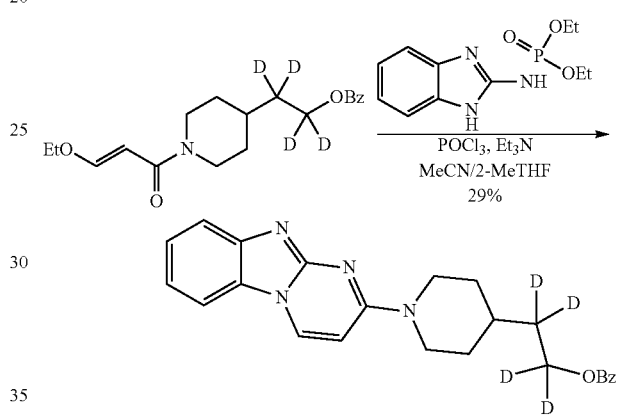

To a solution of diethyl (1H-benzo[d]imidazol-2-yl)phosphoramidate (2.30 g, 8.53 mmol, 1.10 equiv) and (E)-2-(1-(3-ethoxyacryloyl)piperidin-4-yl)ethyl-1,1,2,2-d$_4$ benzoate (2.60 g, 7.75 mmol, 1.00 equiv) in 2-MeTHF (13.0 mL) and MeCN (13.0 mL) at 25° C. was added Et$_3$N (392 mg, 3.88 mmol, 539 µL, 0.50 equiv.) followed by POCl$_3$ (2.61 g, 17.0 mmol, 1.58 mL, 2.20 equiv). The reaction was then heated to 80° C. and stirred for 4 h. Upon confirmation of reaction completion, saturated aqueous NaHCO$_3$ (100.0 mL) was charged and the resulting aqueous layer was extracted with three portions of DCM (100.0 mL). The organic phases were then combined, dried over Na$_2$SO$_4$, and evaporated to dryness. The crude was then slurried in EtOAc (30.0 mL) then filtered. This slurry process was repeated twice more. The resulting solids were then purified by prep-HPLC to afford 2-(1-(benzo[4,5]imidazo[1,2-a]pyrimidin-2-yl)piperidin-4-yl)ethyl-1,1,2,2-d$_4$ benzoate (0.900 g, 2.22 mmol, 29% yield) as a yellow solid.

$^1$H NMR (400 MHz, DMSO-d$_6$): δ ppm 8.94 (d, J=7.82 Hz, 1H), 7.89-8.03 (m, 3H), 7.61-7.72 (m, 1H), 7.45-7.58 (m, 3H), 7.24-7.34 (m, 1H), 7.07-7.19 (m, 1H), 6.89 (d, J=7.82 Hz, 1H), 4.39-4.82 (m, 2H), 3.03 (br t, J=11.55 Hz, 2H), 1.74-1.96 (m, 3H), 1.05-1.34 (m, 2H).

$^{13}$C NMR (400 MHz, DMSO-d$_6$): δ ppm 166.2, 158.3, 152.5, 144.6, 134.8, 133.7, 130.3, 129.5, 129.2, 128.2, 124.5, 119.4, 117.5, 110.6, 96.3, 44.9, 32.9, 32.0.

Examples 3.0-3.5 illustrate representative syntheses of molecules using the underlying step of conjugating an acrylamide with a phosphorylated imidazole.

Example 3.0: Synthesis of 2-amino-imidazo[1,2-a]pyrimidine ($R_1$=$R_2$=$R_3$=$R_4$=H)

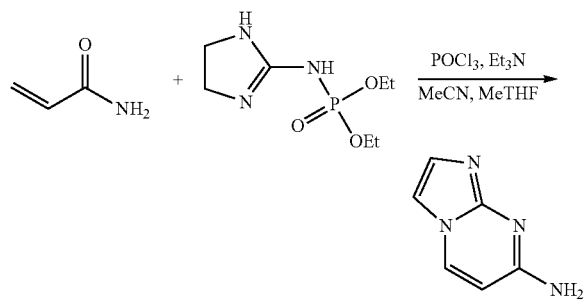

To a vial was combined acrylamide (0.500 mmol, 1.0 equiv), phosphorylated imidazole (0.550 mmol, 1.1 equiv.), 2-Me THF (0.5 mL), and MeCN (0.5 mL). POCl$_3$ (1.1 mmol, 2.2 equiv) was then added to the resulting mixture and the reaction was heated to 80° C. and stirred overnight. The crude reaction mixture was then cooled to 23° C., quenched with 1 mL of Et$_3$N, dry-loaded onto silica gel, and flashed with a 0-10% DCM:MeOH gradient mobile phase.

Example 3.1: Synthesis of 2-(4-phenylpiperidin-1-yl)benzo[4,5]imidazo[1,2-a]pyrimidine

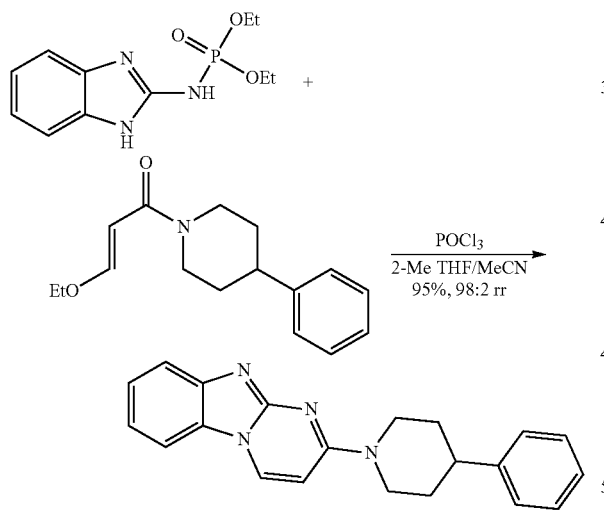

The general procedure was followed using diethyl (1H-benzo[d]imidazol-2-yl)phosphoramidate (0.296 g, 1.10 mmol, 1.1 equiv), (E)-3-ethoxy-1-(4-phenylpiperidin-1-yl)prop-2-en-1-one (0.259 g, 1.00 mmol, 1.0 equiv), and POCl$_3$ (0.204 mL, 2.20 mmol, 2.2 equiv), in 2-Me THF (1.0 mL) and MeCN (1.0 mL). 2-(4-phenylpiperidin-1-yl)benzo[4,5]imidazo[1,2-a]pyrimidine was isolated as an off-white solid (0.312 mg, 95% yield, 98:2 regioisomer ratio) after purification by flash chromatography.

$^1$H NMR (400 MHz, chloroform-d): δ 8.23 (d, J=7.7 Hz, 1H), 7.73 (d, J=8.1 Hz, 1H), 7.55 (d, J=8.0 Hz, 1H), 7.37 (t, J=7.7 Hz, 1H), 7.31 (t, J=7.5 Hz, 2H), 7.26-7.14 (m, 4H), 6.44 (d, J=7.8 Hz, 1H), 4.77 (s, 2H), 3.09 (t, J=13.0 Hz, 2H), 2.85 (tt, J=12.2, 3.8 Hz, 1H), 2.00 (q, J=12.3 Hz, 2H), 1.75 (qd, J=12.8, 4.2 Hz, 2H).

$^{13}$C NMR (101 MHz, chloroform-d): δ 157.9, 152.9, 145.2, 144.9, 132.7, 128.7, 127.9, 126.9, 126.6, 124.8, 119.8, 118.7, 108.8, 95.5, 45.8, 43.0, 33.3.

Example 3.2: Synthesis of 7-(4-phenylpiperidin-1-yl)imidazo[1,2-a]pyrimidine

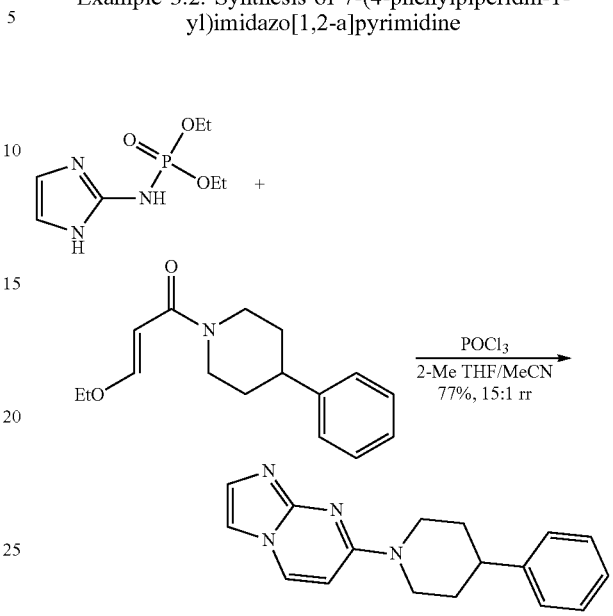

The general procedure was followed using diethyl (1H-imidazol-2-yl)phosphoramidate (0.241 g, 1.10 mmol, 1.1 equiv), (E)-3-ethoxy-1-(4-phenylpiperidin-1-yl)prop-2-en-1-one 0.259 g, 1.00 mmol, 1.0 equiv), and POCl$_3$ (0.186 mL, 2.00 mmol, 2.0 equiv) in 2-Me THF (1.0 mL) and MeCN (1.0 mL). 7-(4-phenylpiperidin-1-yl)imidazo[1,2-a]pyrimidine was isolated as an off-white solid (0.215 g, 77% yield, 15:1 regioisomer ratio) after purification by flash chromatography.

$^1$H NMR (400 MHz, chloroform-d): δ 8.02 (d, J=7.7 Hz, 1H), 7.37 (d, J=1.6 Hz, 1H), 7.34-7.24 (m, 2H), 7.20 (ddd, J=7.8, 5.9, 1.7 Hz, 3H), 7.13 (d, J=1.6 Hz, 1H), 4.64 (d, J=13.4 Hz, 1H), 3.03 (td, J=13.3, 2.6 Hz, 2H), 2.80 (tt, J=12.2, 3.7 Hz, 1H), 1.95 (d, J=12.8 Hz, 2H), 1.72 (qd, J=12.7, 4.1 Hz, 2H).

$^{13}$C NMR (101 MHz, chloroform-d): δ 156.2, 149.9, 145.5, 133.7, 132.5, 128.6, 126.8, 126.5, 108.8, 97.5, 45.8, 43.0, 33.1.

Example 3.3: Synthesis of ethyl 2-(4-phenylpiperidin-1-yl)benzo[4,5]imidazo[1,2-a]pyrimidine-8-carboxylate

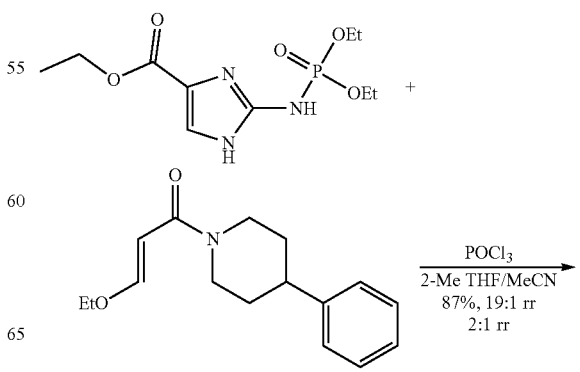

-continued

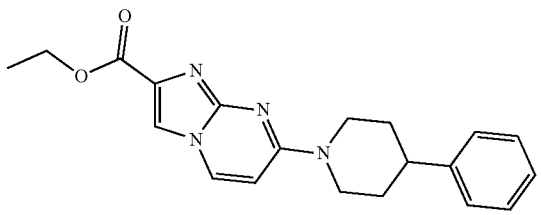

The general procedure was followed using ethyl 2-((diethoxyphosphoryl)amino)-1H-imidazole-4-carboxylate (0.160 g, 0.550 mmol, 1.1 equiv), (E)-3-ethoxy-1-(4-phenylpiperidin-1-yl)prop-2-en-1-one 0.130 g, 0.500 mmol, 1.0 equiv), and POCl$_3$ (0.102 mL, 1.10 mmol, 2.2 equiv) in 2-Me THF (0.5 mL) and MeCN (0.5 mL). 7-(4-phenylpiperidin-1-yl)imidazo[1,2-a]pyrimidine was isolated as an off-white solid (0.152 g, 87% yield, 19:1 regioisomer ratio) after purification by flash chromatography.

$^1$H NMR (400 MHz, chloroform-d): δ 8.02 (d, J=7.8 Hz, 1H), 7.77 (s, 1H), 7.35-7.25 (m, 3H), 7.25-7.15 (m, 3H), 6.55 (d, J=7.8 Hz, 1H), 4.66 (d, J=13.1 Hz, 2H), 4.39 (q, J=7.1 Hz, 2H), 3.07 (td, J=13.2, 2.5 Hz, 2H), 2.83 (tt, J=12.2, 3.7 Hz, 1H), 2.02-1.90 (m, 2H), 1.73 (dtd, J=13.4, 12.4, 4.2 Hz, 3H), 1.40 (t, J=7.1 Hz, 3H).

$^{13}$C NMR (101 MHz, chloroform-d): δ 163.8, 156.6, 149.5, 145.3, 135.9, 133.8, 128.7, 126.9, 126.7, 114.0, 99.4, 60.9, 45.9, 43.0, 33.1, 14.5.

Example 3.4: Synthesis of N-benzylbenzo[4,5]imidazo[1,2-a]pyrimidin-2-amine

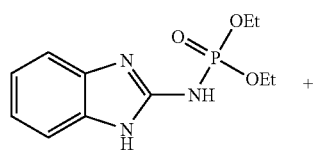

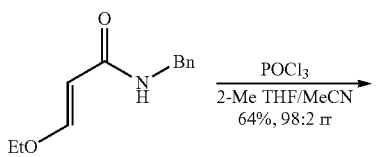

The general procedure was followed using diethyl (1H-benzo[d]imidazol-2-yl)phosphoramidate (0.296 g, 1.10 mmol, 1.1 equiv), (E)-N-benzyl-3-ethoxyacrylamide (0.205 g, 1.00 mmol, 1.0 equiv), POCl$_3$ (0.204 mL, 1.10 mmol, 2.1 equiv), in 2-Me THF (0.5 mL) and MeCN (0.5 mL). N-benzylbenzo[4,5]imidazo[1,2-a]pyrimidin-2-amine was isolated as an off-white solid (0.175 g, 64% yield, 98:2 regioisomer ratio) after purification by flash chromatography.

$^1$H NMR (400 MHz, DMSO-d6): δ 8.82 (d, J=7.4 Hz, 1H), 8.39 (t, J=5.8 Hz, 1H), 7.88 (d, J=7.9 Hz, 1H), 7.50 (d, J=8.0 Hz, 1H), 7.44-7.31 (m, 4H), 7.31-7.23 (m, 2H), 7.15 (t, J=7.6 Hz, 1H), 6.43 (d, J=7.3 Hz, 1H), 4.65 (d, J=5.6 Hz, 2H).

$^{13}$C NMR (101 MHz, DMSO-d6): δ 158.8, 152.4, 143.8, 138.9, 133.3, 128.4, 128.0, 127.57, 127.0, 123.9, 119.2, 117.2, 109.9, 99.2, 43.6.

Example 3.5: Synthesis of N,N-dibenzylbenzo[4,5]imidazo[1,2-a]pyrimidin-2-amine

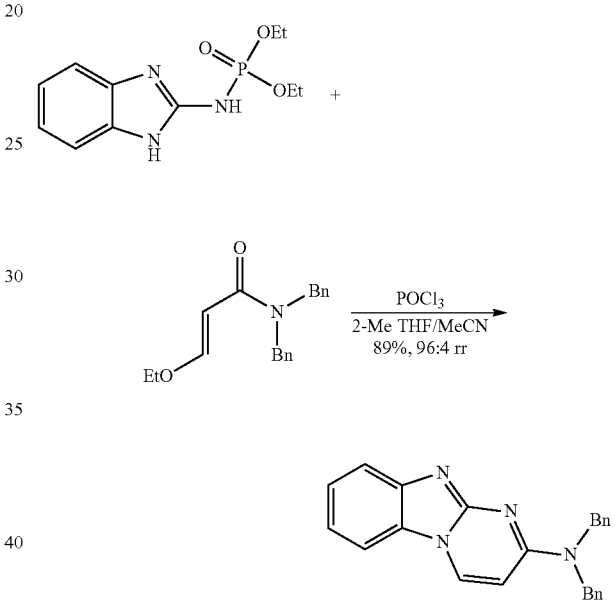

The general procedure was followed using diethyl (1H-benzo[d]imidazol-2-yl)phosphoramidate (0.148 g, 0.550 mmol, 1.1 equiv), (E)-N,N-dibenzyl-3-ethoxyacrylamide (0.148 g, 0.500 mmol, 1.0 equiv), POCl$_3$ (0.102 mL, 1.10 mmol, 2.1 equiv), in 2-Me THF (0.5 mL) and MeCN (0.5 mL). N,N-dibenzylbenzo[4,5]imidazo[1,2-a]pyrimidin-2-amine was isolated as an off-white solid (163 mg, 89% yield, 96:4 regioisomer ratio) after purification by flash chromatography.

1H NMR (400 MHz, chloroform-d): δ 8.21 (d, J=7.6 Hz, 1H), 7.76 (d, J=8.1 Hz, 1H), 7.54 (d, J=8.0 Hz, 1H), 7.42-7.23 (m, 11H), 7.19 (t, J=7.6 Hz, 1H), 6.29 (d, J=7.7 Hz, 1H), 5.09-4.69 (bs, 4H).

$^{13}$C NMR (101 MHz, chloroform-d): δ 159.1, 144.9, 133.0, 129.0, 127.8, 127.8, 125.0, 120.0, 118.9, 110.1, 108.9, 96.0, 51.1.

Example 4: Optimization of the Annulation Reaction

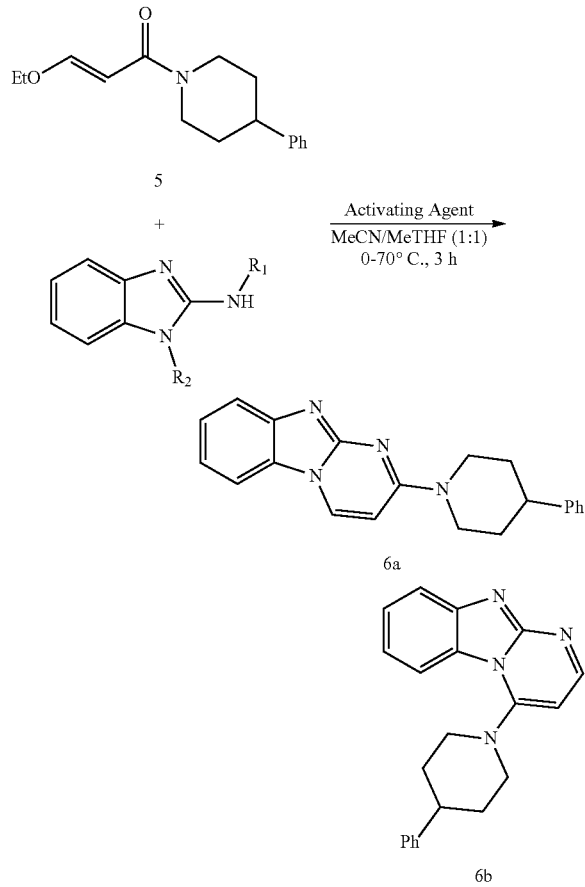

We began by exploring the annulation of 2-aminobenzimidazole and the acrylamide (5) under thermal conditions (70° C.) and observed low conversion and no desired product (Table 1, entry 1). Activation of the amide to the corresponding imidoyl chloride provided the necessary increase in reactivity. Both $PCl_5$ (Table 1, entry 2) and $POCl_3$ (Table 1, entry 3) were found to be effective activating reagents, with $POCl_3$ providing product in 71% yield but in a superior 75:25 ratio of isomers 6a:6b. We then found that subjecting both reaction partners to activation by $POCl_3$ independently, and then combining the reaction streams, significantly increased the isomeric selectivity to 90:10 (Table 1, entry 4). However, this protocol proved difficult to reproduce and was operationally cumbersome. Analysis of the reaction mixture of 2-aminobenzimidazole and $POCl_3$ by LCMS suggested the formation of multiple N-phosphorylated products.

We hypothesized that phosphoramidate(s) could act as isolable analogue(s) to the transiently generated N-phosphorylated species, and to this end synthesized substrates 2a and 2b (FIG. 1) (see, for example, Bandyopadhyay, P.; Sathe, M.; Tikar, S. N; Yadav, R.; Sharma, P.; Kumar, A.; Kaushik, M. P. Synthesis of some novel phosphorylated and thiophosphorylatedbenzimidazoles and benzothiazoles and their evaluation for larvicidal potential to Aedes albopictus and Culex quinquefasciatus, *Bioorg. Med. Chem. Lett.*, 2014, 24, 2934-2939). Diethyl phosphoramidate 2a in particular provided a clean reaction profile and 98:2 selectivity for isomer 6a (Table 1, entry 5). Isomeric phosphoramidate 2b inverted product selectivity to favor 6b, albeit in slightly diminished yields and selectivity (Table 1, entry 7) that were both improved upon further optimization (Table 1, entry 8; see also Example 7).

TABLE 1

Optimization of the Annulation Reaction

| Entry[a] | Activating Agent | Aminoimidazole | $R_1$ | $R_2$ | A % (6a + 6b)[b] | 6a:6b[c] |
|---|---|---|---|---|---|---|
| 1 | none | 1 | H | H | 0 | — |
| 2 | $PCl_5$ | 1 | H | H | 84 | 55:45 |
| 3 | $POCl_3$ | 1 | H | H | 71 | 75:25 |
| 4[d] | $POCl_3$ | 1 | H | H | 89 | 90:10 |
| 5 | $POCl_3$ | 2a | $P(O)(OEt)_2$ | H | 96 | 98:2 |
| 6 | $POCl_3$ | 4 | $P(O)(OPh)_2$ | H | 92 | 98:2 |
| 7 | $POCl_3$ | 3 | H | $P(O)(OEt)_2$ | 68 | 20:80 |
| 8[e] | $POCl_3$ | 3 | H | $P(O)(OEt)_2$ | 94 | 4:96 |

[a] Reactions were performed on a 0.25 mmol scale, acrylamide (1.0 equiv), aminobenzimidazole (1.1 equiv), activating agent (2.2 equiv), 0.5 M.

[b] A % = HPLC area percent at 254 nm.

[c] Ratios of 6a:6b determined by HPLC analysis of the crude reaction mixture at 254 nm.

[d] Both 1 and 2b were allowed to react with $POCl_3$ at 0° C. for 30 min. prior to being combined and then heated to 70° C.

[e] 5 was pretreated with $POCl_3$, heated to 70° C. for 20 min., and then cooled to rt prior to being added to 3.0 equiv. 2b. Then the reaction mixture was heated to 50° C.

Figure 2:
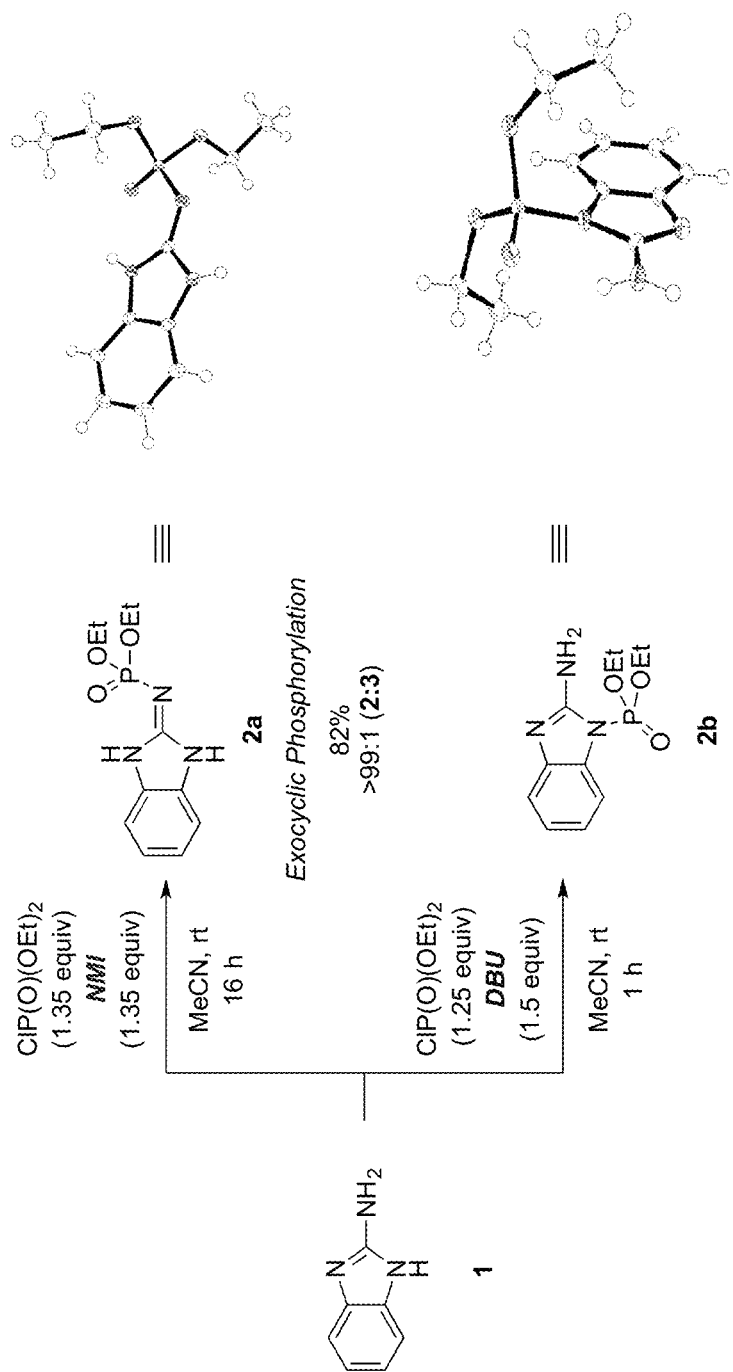
FIG. 2: Selective access to phosphoramidates.

We note that both isomeric phosphoramidates may be accessed in high selectivity from 2-aminobenzimidazole (1), and that the choice of base in the phosphorylation reaction dictates the product selectivity. We found that the use of N-methylimidazole (NMI) provides the exocyclic phosphorylated product 2a in a >99:1 ratio vs. 2b. Conversely, employing 1,8-diazabicyclo[5.4.0]undec-7-ene (DBU) as base provided the complementary endocyclic phosphorylated product 2b in 99:1 isomeric selectivity. This divergent phosphorylation in turn provides the foundation to access both 2- and 4-amino ben-zo[4,5]imidazo[1,2-a]pyrimidines. The structures of phosphoramidates 2a and 2b were confirmed by X-ray crystallographic analysis (FIG. 2).

Example 5: Variations of β-Ethoxy Acrylamides

Figure 3:
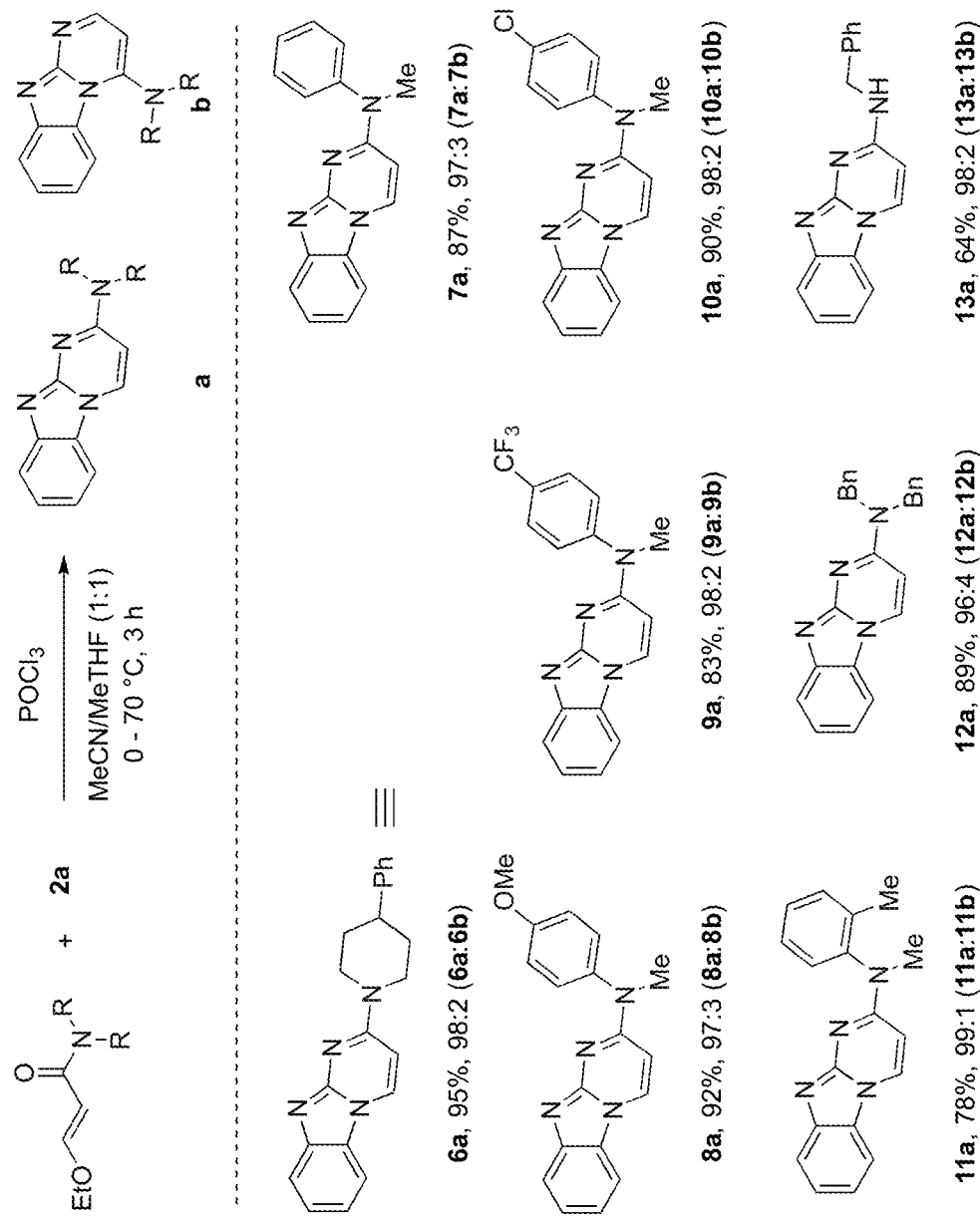
FIG. 3. Examples of β-ethoxy acrylamides used to generate benzo[4,5]imidazo[1,2-a]pyrimidin-2-amines.

Upon the discovery of suitable conditions to selectively prepare 2- or 4-aminobenzimidazo[1,2-a]pyrimidines, we explored the scope of the reaction. A variety of β-ethoxy acrylamides were evaluated in condensations with phosphoramidate 2a under the standard reaction conditions (as shown in FIG. 3). These pairings indeed generated benzo [4,5]imidazo[1,2-a]pyrimidin-2-amines as the predominant products, as ascertained by X-ray crystallographic analysis of 6a (see Example 46).

We noted that various secondary acrylamides reacted smoothly to furnish the annulation products in good yields and excellent selectivities. Both aryl and aliphatic N-substituted acrylamides were well-tolerated, and there was no discernable electronic effect on outcome. When a primary acrylamide was employed in the reaction (compound 13a in FIG. 3), the reaction produced several undesired side products and consequently the isolated yield suffered.

In FIG. 3, reactions were performed on either 0.5 or 1.0 mmol scale, acrylamide (1.0 equiv), 2 (1.1 equiv.), POCl$_3$ (2.2 equiv.), 0.5 M. Quoted yields are isolated yield after silica gel chromatography. The reported ratios of a:b isomers were determined via HPLC analysis by uncorrected A % of the crude reaction mixture at 254 nm.

Example 6: Variations of amino(benz)imidazole

Figure 4:
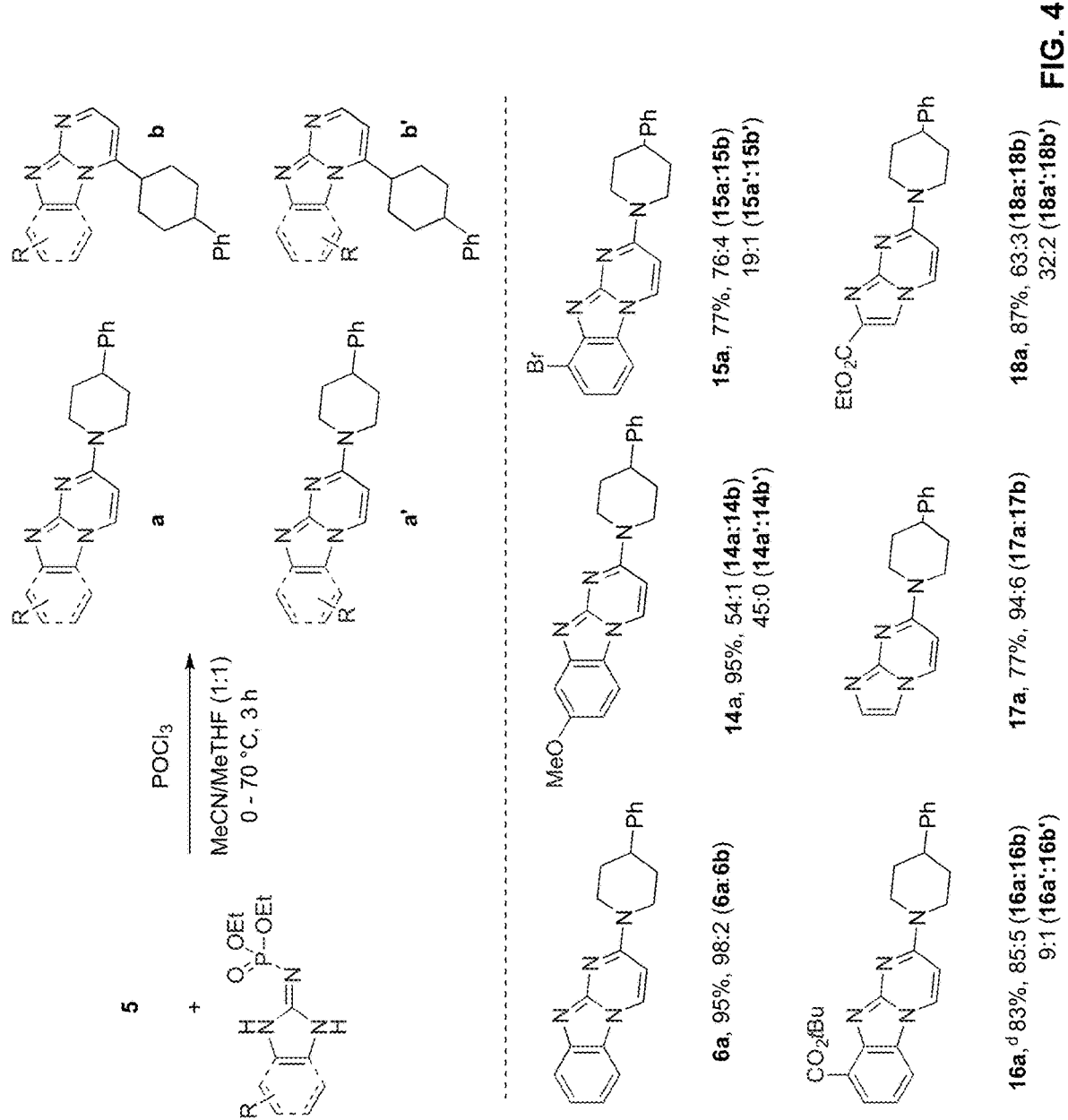
FIG. 4. Examples of amino(benz)imidazole to furnish benzo[4,5]imidazo[1,2-a]pyrimidin-2-amines.

A variety of other N2-phosphorylated amino-imidazoles were utilized in the annulation reaction (FIG. 4). Under similar reaction conditions, both electron-rich and electron-deficient amino-benzimidazole derivatives reacted in 77-95% yields, with 94:6 selectivity for the 2-amino-imidazo[1,2-a]pyrimidine isomeric products.

In FIG. 4, reactions were performed on 0.5 mmol scale, acrylamide (1.0 equiv), 2a (1.1 equiv), POCl$_3$ (2.2 equiv), 0.5 M. The quoted yields are isolated yields after silica gel chromatography. The ratios of a:a':b:b' were determined via HPLC analysis by uncorrected A % of the crude reaction mixture at 254 nm. Et$_3$N (1.5 equiv.) was added to the reaction that formed 16a (and its isomers).

As can be seen, the use of unsymmetrically substituted amino-imidazoles in the reaction can give rise to another set of constitutional isomers based on which nitrogen of the imidazole ring engages in C—N bond formation, as shown in FIG. 4 and denoted a vs. a' and b vs. b'. When a sterically demanding substituent is located in the 4-position of the phosphoramidate (FIG. 4, 16a:16a') a 90:10 ratio of isomeric products was obtained. The substrate arising from 2-amino-6-methoxybenzimidazole provides poor selectivity under these conditions (FIG. 4, 14a:14a'=55:45).

The reaction conditions may be buffered with the use of 1.5 equiv. of Et$_3$N to allow for the coupling of substrates bearing acid-sensitive functional groups (such as for product 16a).

Example 7: Formation of 4-aminoimidazo[1,2-a]pyrimidines

This example addresses formation of 4-aminoimidazo[1,2-a]pyrimidine products via the condensation of acrylamides with N1 phosphoramidate 2b.

An initial experiment in which all reagents were combined together and POCl$_3$ was added last resulted in an 80:20 ratio of 6b:6a (Table 1, entry 7). LCMS of the crude reaction mixture showed a significant amount of 2-aminobenzimidazole 1, which indicated the decomposition of 2b under the reaction conditions.

Figure 5:
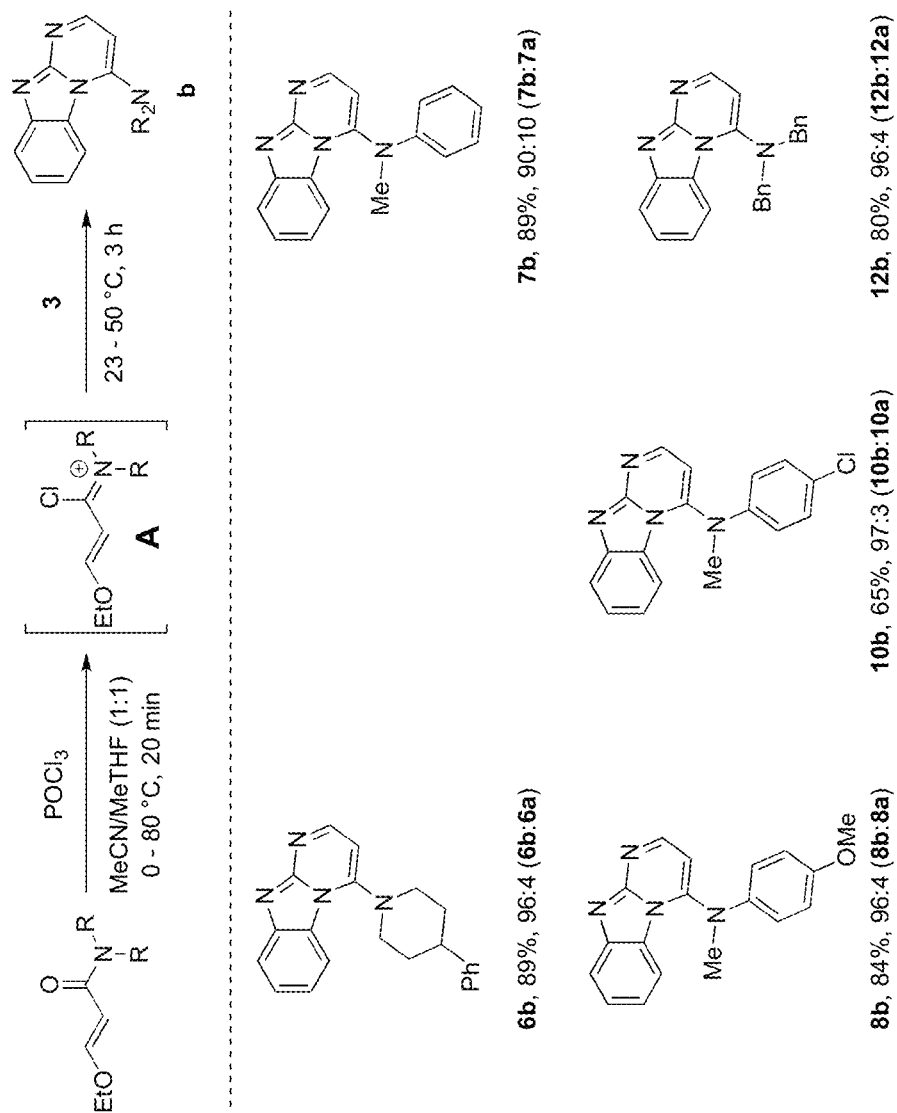
FIG. 5. Examples of β-ethoxy acrylamides in reactions with phosphoramidate 3 to prepare benzo[4,5]imidazo[1,2,a]pyrimidin-4-amines.

It is possible that the pre-formation of the possible imidoyl chloride intermediate A, by pretreating 5 with POCl$_3$ followed by addition of 3, could outcompete the decomposition pathway (FIG. 5). Such a protocol proved beneficial, and product was isolated in 89% yield and 96:4 ratio of 6b:6a (Table 1, entry 8).

We then explored the annulation of a variety of acrylamides with phosphoramidate 3 to access various 4-amino isomers (FIG. 5) using the protocol from Table 1, entry 8. In FIG. 5, reactions were performed on 0.5 mmol scale, acrylamide (1.0 equiv), 3 (3.0 equiv), POCl$_3$ (1.2 equiv), 0.5 M. Isolated yields were reported after silica gel chromatography. The reported ratios of a:b isomers were determined via HPLC analysis by uncorrected A % of the crude reaction mixture at 254 nm.

Good yields were observed with aliphatic secondary β-ethoxy acrylamides and with electron-rich aryl acrylamides. However, the use of an electron-deficient acrylamide led to yields of product 10b that were significantly less than other starting materials. Isomeric selectivities were ≥90:10 of b:a across all substrates.

Examples 8-13 illustrate procedures for the synthesis of various phosphoramidates. Not all of the structures depicted correspond to actual X-ray structures but instead were based on the X-ray confirmed structure of 2a, as shown in Example 44.

Example 8: Diethyl (2-amino-1H-benzo[d]imidazol-1-yl)phosphonate (2b)

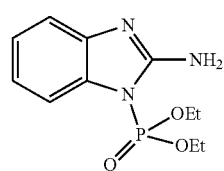

2b

Example 9: Diethyl (Z)-(5-methoxy-1,3-dihydro-2H-benzo[d]imidazol-2-ylidene)phosphoramidate (19)

To a 40 mL scintillation vial containing a stir bar was added 1H-benzimidazol-2-amine (2.00 g, 15.0 mmol, 1.00 equiv) and the reaction was capped with a septum cap. Acetonitrile (16 mL) was added followed by 1,8-diazabicyclo[5.4.0]undec-7-ene (3.40 mL, 22.5 mmol, 1.50 equiv). Diethyl chlorophosphate (2.70 mL, 18.8 mmol, 1.25 equiv.) was added in one portion at rt. The reaction was then allowed to stir at rt for 1 hour. The reaction mixture was concentrated onto silica gel (10.0 g) via rotary evaporation and then filtered through silica gel (20.0 g) using dichloromethane (100 mL) as eluent. The resulting colorless solution was concentrated to dryness under vacuum. Diethyl (2-amino-1H-benzo[d]imidazol-1-yl)phosphonate (3) was isolated as a white solid in 96% yield (3.90 g, 14.3 mmol): m.p. 74-79° C.; FTIR (neat cm$^{-1}$) 1680, 1477, 1192, 1027, 931, 789, 738; $^1$H NMR (400 MHz, chloroform-d) δ 7.32 (dd, J=13.3, 7.9 Hz, 2H), 7.16 (t, J=7.7 Hz, 1H), 7.02 (t, J=7.7 Hz, 1H), 6.61 (s, 2H), 4.33-4.17 (m, 2H), 4.17-3.96 (m, 2H), 1.31 (t, J=7.1 Hz, 6H). $^{13}$C NMR (101 MHz, chloroform-d) δ 155.7 (d, J=5.8 Hz), 143.9 (d, J=13.1 Hz), 132.3 (d, J=5.0 Hz), 123.9, 120.5, 116.2, 111.5, 64.6 (d, J=4.6 Hz), 16.0 (d, J=7.2 Hz). $^{31}$P NMR (162 MHz, chloroform-d) δ −4.72. HRMS: calcd for $C_{11}H_{17}N_3O_3P$ [M+H]$^+$ =270.1002, observed=270.0998.

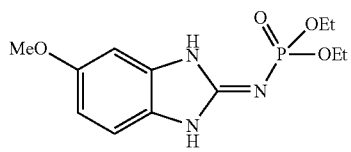

19

To a 20 mL scintillation vial with a stir bar was added 5-methoxy-1H-benzimidazole-2-ylamine (1.00 g, 5.80 mmol, 1.00 equiv) and acetonitrile (1.0 M, 5.8 mL) followed by N-methylimidazole (0.693 mL, 8.70 mmol, 1.50 equiv). The vial was capped with a septum cap and diethyl chlorophosphate (1.25 mL, 8.70 mmol, 1.50 equiv) was slowly added (via syringe pump) over 30 minutes at rt. The reaction was allowed to stir at rt for 18 hours. After stirring overnight at rt, MTBE (3.0 mL) was added and the reaction mixture was filtered. The filter cake was then dried under vacuum at rt with a nitrogen flow for 4 hours followed by drying in a vacuum oven at 40° C. for 24 hours. Desired product, diethyl (Z)-(5-methoxy-1,3-dihydro-2H-benzo[d]imidazol-2-ylidene)phosphoramidate (19) was isolated as a yellow solid (0.75 g, 43%): m.p. 205-208° C.; FTIR (neat cm$^{-1}$) 1664, 1611, 1206, 1056, 952, 801, 700; $^1$H NMR (400 MHz, DMSO-d$_6$) δ 11.09 (bs, 2H), 7.06 (d, J=8.6 Hz, 1H), 6.78 (d, J=2.4 Hz, 1H), 6.62 (dd, J=8.6, 2.4 Hz, 1H), 3.98-3.84 (m, 4H), 3.71 (s, 3H), 1.21 (td, J=7.1, 0.7 Hz, 6H). $^{13}$C NMR (101 MHz, DMSO-d$_6$) δ 155.0, 152.3 (d, J=7.1 Hz), 130.8, 124.0, 110.3, 107.9, 96.0, 60.9 (d, J=5.9 Hz), 55.5, 16.2 (d, J=6.6 Hz). $^{31}$P NMR (162 MHz, DMSO-d$_6$) δ 7.35. HRMS: calcd for $C_{12}H_{19}N_3O_4P$ [M+H]$^+$: 300.1108; found: 300.1105.

Example 10: Diethyl (Z)-(4-bromo-1,3-dihydro-2H-benzo[d]imidazol-2-ylidene)phosphoramidate (20)

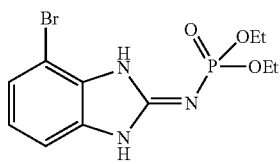

20

To a 20 mL scintillation vial with a stir bar was added 4-bromo-1H-benzo[d]imidazol-2-amine (1.97 g, 9.40 mmol, 1.00 equiv) and acetonitrile (1.0 M, 9.4 mL) followed by N-methylimidazole (1.00 mL, 12.7 mmol, 1.35 equiv). The vial was capped with a septa cap and diethyl chlorophosphate (1.83 mL, 12.7 mmol, 1.35 equiv) was added via syringe pump over 30 min at rt. The reaction was allowed to stir at rt for 18 hours. After stirring overnight at rt, the mixture was dry loaded onto silica gel and purified via automated silica gel chromatography using 0-10% CH$_3$OH in CH$_2$Cl$_2$ as eluent. Desired product, diethyl (Z)-(4-bromo-1,3-dihydro-2H-benzo[d]imidazol-2-ylidene)phosphoramidate (20) was isolated as a white solid (1.50 g, 46%): m.p. 154-156° C.; FTIR (neat cm$^{-1}$) 1648, 1535, 1431, 1253, 1009, 741, 665, 571, 526; $^1$H NMR (400 MHz, DMSO-d$_6$) δ 7.30 (dd, J=8.0, 0.9 Hz, 1H), 7.27-7.18 (m, 3H), 6.91 (t, J=8.0 Hz, 1H), 4.21 (ddq, J=10.3, 9.2, 7.1 Hz, 2H), 4.09 (ddq, J=10.3, 8.9, 7.0 Hz, 2H), 1.22 (td, J=7.1, 0.8 Hz, 6H). $^{13}$C NMR (101 MHz, DMSO-d$_6$) δ 155.7 (d, J=5.1 Hz), 142.8 (d, J=13.1 Hz), 132.6 (d, J=5.1 Hz), 126.0, 120.9, 110.6, 107.8, 64.7 (d, J=5.0 Hz), 15.7 (d, J=6.5 Hz). $^{31}$P NMR (162 MHz, DMSO-d$_6$) δ −5.22. HRMS: calcd for $C_{11}H_{16}BrN_3O_3P$ [M+H]$^+$: 348.0107; found: 348.0089.

Example 11: tert-Butyl (Z)-2-((diethoxyphosphoryl)imino)-2,3-dihydro-1H-benzo[d]imidazole-4-carboxylate (21)

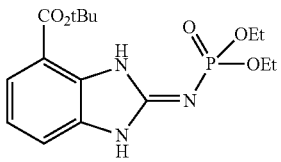

21

To a 20 mL scintillation vial with a stir bar was added tert-butyl 2-amino-1H-benzo[d]imidazole-4-carboxylate (0.700 g, 5.15 mmol, 1.00 equiv) and acetonitrile (1.0 M, 5.2 mL) followed by N-methylimidazole (0.550 mL, 7.00 mmol, 1.35 equiv). The vial was capped with a septum cap and diethyl chlorophosphate (1.00 mL, 5.15 mmol, 1.35 equiv) was added via syringe pump over 30 min at rt. The reaction was allowed to stir at rt for 18 hours. After stirring overnight at rt, the mixture was dry loaded onto silica gel and purified via automated silica gel chromatography using 0-10% CH$_3$OH in CH$_2$Cl$_2$ as eluent. Desired product, diethyl (Z)-(5-methoxy-1,3-dihydro-2H-benzo[d]imidazol-2-ylidene)phosphoramidate (21) was isolated as a white solid (0.70 g, 37%): m.p. 192-199° C.; FTIR (neat cm$^{-1}$) 1690, 1644, 1458, 1366, 1289, 1145, 1049, 923, 747; $^1$H NMR (400 MHz, DMSO-d$_6$) δ 11.16 (s, 1H), 10.83 (s, 1H), 7.53 (dd, J=8.0, 1.1 Hz, 1H), 7.35 (dd, J=7.8, 1.1 Hz, 1H), 7.15 (t, J=7.9 Hz, 1H), 4.07-3.83 (m, 4H), 1.60 (s, 9H), 1.22 (td, J=7.0, 0.7 Hz, 6H). $^{13}$C NMR (101 MHz, DMSO-d$_6$) δ 164.2, 150.0, 129.9, 122.2, 121.5, 82.0, 61.3 (d, J=5.6 Hz), 27.9, 16.1 (d, J=6.7 Hz). $^{31}$P NMR (162 MHz, DMSO-d$_6$) δ 9.20. HRMS: calcd for $C_{16}H_{25}N_3O_5P$ [M+H]$^+$: 370.1526; found: 370.1513.

Example 12: Diethyl (1,3-dihydro-2H-imidazol-2-ylidene)phosphoramidate (22)

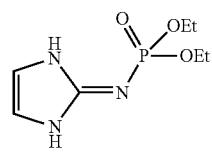

22

To a 20 mL scintillation vial with a stir bar was added 1H-imidazol-2-amine (0.662 g, 8.00 mmol, 1.00 equiv) and acetonitrile (8 mL, 1.0 M) followed by N-methylimidazole (0.860 mL, 10.8 mmol, 1.35 equiv). The vial was capped with a septum cap and diethyl chlorophosphate (1.56 mL, 10.8 mmol, 1.35 equiv) was slowly added (via syringe pump) over 30 minutes at rt. The reaction was allowed to stir at rt for 18 hours. After stirring at rt for 18 hours the reaction was dry loaded onto silica gel and purified via automated silica gel chromatography with a gradient of 0-10% $CH_3OH$ in $CH_2Cl_2$. Diethyl (1,3-dihydro-2H-imidazol-2-ylidene)phosphoramidate (22) was isolated as a white solid (0.41 g, 24%): m.p. 155-166° C.; FTIR (neat $cm^{-1}$) 1638, 1572, 1182, 1023, 906, 960; $^1H$ NMR (400 MHz, chloroform-d) δ 11.10 (bs, 2H), 6.44 (s, 2H), 4.03 (pd, J=7.1, 1.6 Hz, 4H), 1.29 (t, J=7.1 Hz, 6H). $^{13}C$ NMR (101 MHz, chloroform-d) δ 150.7 (d, J=6.7 Hz), 111.5, 61.9 (d, J=5.6 Hz), 16.5 (d, J=7.7 Hz). $^{31}P$ NMR (162 MHz, chloroform-d) δ 10.06. HRMS: calcd for $C_7H_{15}N_3O_3P$ [M+H]$^+$: 220.0846; found: 220.0844.

Example 13: Ethyl (Z)-2-((diethoxyphosphoryl)imino)-2,3-dihydro-1H-imidazole-4-carboxylate (23)

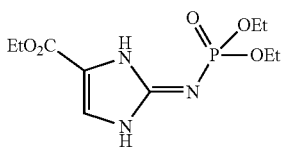

23

To a 20 mL scintillation vial with a stir bar was added ethyl 2-amino-1H-imidazole-4-carboxylate (0.759 g, 4.90 mmol, 1.00 equiv) and acetonitrile (4.9 mL, 1.0 M) followed by N-methylimidazole (0.600 mL, 7.30 mmol, 1.35 equiv). The vial was capped with a septum cap and diethyl chlorophosphate (1.10 mL, 7.30 mmol, 1.35 equiv) was slowly added (via syringe pump) over 30 minutes at rt. The reaction was allowed to stir at rt for 18 hours. After stirring at rt for 18 hours the reaction was dry loaded onto silica gel and purified via automated silica gel chromatography with a gradient of 0-10% $CH_3OH$ in $CH_2Cl_2$. Ethyl (Z)-2-((diethoxyphosphoryl)imino)-2,3-dihydro-1H-imidazole-4-carboxylate (S5) was isolated as a white solid (0.44 g, 31%): m.p. 114-118° C.; FTIR (neat $cm^{-1}$) 1701, 1642, 1591, 1441, 1326, 1179, 1154, 1028, 955; $^1H$ NMR (400 MHz, Chloroform-d) δ 10.72 (bs, 2H), 7.33 (s, 1H), 4.31 (q, J=7.1 Hz, 2H), 4.13 (pd, J=7.3, 5.0 Hz, 4H), 1.33 (m, 9H). $^{13}C$ NMR (101 MHz, chloroform-d) δ 160.6, 147.8, 124.5, 121.3, 63.3 (d, J=5.3 Hz), 60.8, 16.3 (d, J=6.9 Hz), 14.5. $^{31}P$ NMR (162 MHz, chloroform-d) δ 4.43. HRMS: calcd for $C_{10}H_{19}N_3O_6P$ [M+H]$^+$: 292.1057; found: 292.1046.

Examples 14-21 illustrate procedures for the synthesis of various acrylamides.

Example 14: (E)-3-Ethoxy-1-(4-phenylpiperidin-1-yl)prop-2-en-1-one (24)

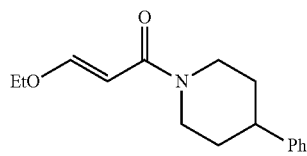

24

To a 400 mL reactor equipped with overhead agitation under an active nitrogen line at rt was combined (E)-3-ethoxyprop-2-enoic acid (9.42 g, 80.6 mmol, 1.30 equiv), 4-phenylpiperidine (10.0 g, 62.0 mmol, 1.00 equiv), 2-PrOH (50 mL, 5.0 mL/g), Et$_3$N (34.6 mL, 248 mmol, 4.00 equiv), then 50 wt % T3P® in ethyl acetate (44.6 mL, 74.4 mmol, 1.2 equiv) in that order (caution: exothermic temperature increase). The reaction was heated to 40° C. for 1 h then quenched with distilled water (150 mL, 15.0 mL/g). The layers were separated, the aqueous layer was extracted twice with DCM (100 mL, 10 mL/g), and then the organic layers were combined. The combined organic layer was then dried over sodium sulfate, filtered, then concentrated under reduced pressure. The crude residue was purified by flash chromatography on silica gel, eluted with a 25-50% IPAc:heptane gradient mobile phase, then concentrated to give the product as a light yellow oil (84%) that upon concentration under high vacuum, formed a white solid:
m.p. 112-114° C. $^1H$ NMR (400 MHz, DMSO-d$_6$) δ 7.43 (d, J=11.9 Hz, 1H), 7.33-7.25 (m, 2H), 7.25-7.14 (m, 3H), 5.90 (d, J=11.9 Hz, 1H), 3.94 (q, J=7.0 Hz, 2H), 2.75 (tt, J=12.1, 3.6 Hz, 1H), 1.83-1.73 (m, 3H), 1.47 (dd, J=12.7, 4.0 Hz, 2H), 1.24 (t, J=7.0 Hz, 3H). $^{13}C$ NMR (101 MHz, DMSO-d$_6$) δ 164.9, 160.6, 145.7, 128.7, 126.7, 126.1, 95.9, 66.7, 42.0, 33.2, 14.5. LRMS: calcd for $C_{16}H_{22}NO_2$ [M+H]$^+$: 260.2; found: 260.2.

Example 15: (E)-3-Ethoxy-N-methyl-N-phenylacrylamide (25)

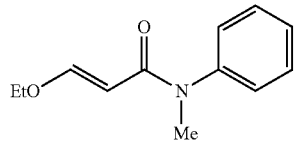

25

To a solution of 1-methylpiperazine (2.81 g, 28.0 mmol. 1.00 equiv) in THF (30 mL, 10.0 mL/g) at rt was added (E)-3-ethoxyprop-2-enoic acid (2.92 g, 25.1 mmol, 0.90 equiv), Et$_3$N (11.7 mL, 84.1 mmol, 3.00 equiv), and 50 w % T3P® in ethyl acetate (27.0 g, 42.4 mmol, 1.50 equiv) in that order. After 22 h at rt, H$_2$O (300 mL, 100.0 mL/g) and ethyl acetate (300 mL, 100.0V) were added to the mixture. The organic layer was separated then concentrated. The residue was purified by flash chromatography on silica gel and eluted with a mixture of petroleum ether/EtOAc (3/1) to afford the product as a light yellow oil (3.85 g, 67%): $^1$H NMR (400 MHz, chloroform-d) δ 7.44 (d, J=12.0 Hz, 1H), 7.31 (t, J=7.4 Hz, 2H), 7.23 (t, J=7.8 Hz, 1H), 7.10 (d, J=7.6 Hz, 2H), 5.06 (d, J=12.0 Hz, 1H), 3.66 (q, J=7.1 Hz, 2H), 3.23 (s, 3H), 1.15 (t, J=7.1 Hz, 3H). $^{13}$C NMR (100 MHz, chloroform-d): 167.1, 160.4, 144.0, 129.4, 127.4, 127.2, 97.5, 67.1, 36.9, 14.5. HRMS calcd for $C_{12}H_{16}O_2N$ [M+H]$^+$: 206.1181; found: 206.1181.

Example 16: (E)-3-Ethoxy-N-(4-methoxyphenyl)-N-methylacrylamide (26)

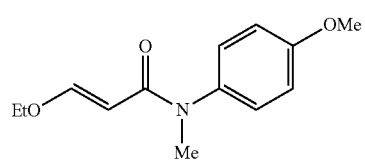

26

To a solution of 4-methoxy-N-methyl-aniline (4.50 g, 32.8 mmol, 1.00 equiv) in THF (45 mL, 10.0 mL/g) at rt was added E)-3-ethoxyprop-2-enoic acid (4.20 g, 36.1 mmol, 1.10 equiv), Et$_3$N (13.7 mL, 98.4 mmol, 3.0 equiv), and 50% T3P® in ethyl acetate (31.3 g, 49.2 mmol, 1.50 equiv) in that order. After 2 h at rt, saturated aqueous Na$_2$CO$_3$ (400 mL 88.9 mL/g) and ethyl acetate (400 mL, 88.9 mL/g) were added to the mixture. The organic layer was separated then concentrated. The residue was purified by flash chromatography on silica gel and eluted with a mixture of petroleum ether/EtOAc (3/1) to afford the product as a light yellow oil (3.10 g, 40%): $^1$H NMR (400 MHz, chloroform-d) δ 7.42 (d, J=12.0 Hz, 1H), 7.12-6.97 (m, 2H), 6.93-6.76 (m, 2H), 5.04 (br d, J=12.2 Hz, 1H), 3.74 (s, 3H), 3.71-3.61 (m, 2H), 3.19 (s, 3H), 1.24-1.07 (m, 3H). $^{13}$C NMR (100 MHz, chloroform-d) 167.4, 160.3, 158.6, 136.9, 128.6, 114.6, 97.5, 67.1, 55.5, 37.2, 14.6. HRMS cacld for $C_{13}H_{18}O_3N$ [M+H]$^+$: 236.1287; found: 236.1288.

Example 17: (E)-3-Ethoxy-N-methyl-N-(4-(trifluoromethyl)phenyl)acrylamide (27)

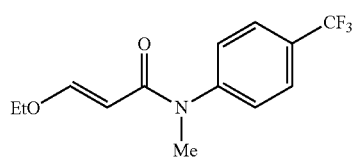

27

To a solution of (E)-3-ethoxyprop-2-enoic acid (2.33 g, 20.1 mmol, 1.00 equiv) in DCM (35 mL, 15.2 mL/g) at rt was added DMF (1.50 mL, 19.5 mmol, 1.00 equiv). Oxalyl chloride (2.57 mL, 29.9 mmol, 1.50 equiv) was then added drop-wise over a period of 0.5 h. The resulting solution was aged at rt for 3 h then concentrated to dryness under reduced pressure. The crude residue was then dissolved in dry DCM (21 mL, 9.0 mL/g). This crude solution was then added drop-wise to a solution of N-methyl-4-(trifluoromethyl) aniline (3.5 g, 20.0 mmol, 1.0 equiv), Et$_3$N (7.0 mL, 50.3 mmol, 2.5 equiv), and DCM (21 mL, 9.0 mL/g) at rt. After 2 h at rt, H$_2$O (200 mL, 87.0 mL/g) and DCM (200 mL, 87.0 mL/g) were added into the mixture. The organic layer was separated then concentrated. The residue was purified by flash chromatography on silica gel, eluted with a mixture of petroleum ether/EtOAc (6/1), then further purified by prep-TLC to afford the product as a light yellow oil (1.50 g, 27%): $^1$H NMR (400 MHz, chloroform-d) δ =7.58 (d, J=8.3 Hz, 2H), 7.48 (d, J=12.0 Hz, 1H), 7.25 (d, J=8.3 Hz, 2H), 5.06 (d, J=12.0 Hz, 1H), 3.72 (q, J=7.1 Hz, 2H), 3.26 (s, 3H), 1.18 (t, J=7.1 Hz, 3H). $^{13}$C NMR (100 MHz, chloroform-d) 161.4, 147.3, 147.3, 129.3, 129.0, 126.6 (q, J=3.9 Hz), 127.6, 122.5, 97.2, 67.5, 53.4, 36.9, 14.6. HRMS calcd for $C_{13}H_{15}O_2NF_3$ [M+H]$^+$: 274.1055; found: 274.1055.

Example 18: (E)-N-(4-Chlorophenyl)-3-ethoxy-N-methylacrylamide (28)

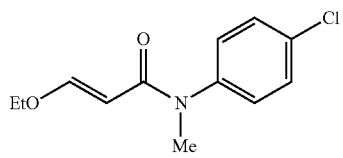

28

To a solution of 4-chloro-N-methyl-aniline (4.50 g, 31.8 mmol, 1.00 equiv) in THF (45 mL, 10.0 mL/g) at rt was added 3-ethoxyprop-2-enoic acid (3.69 g, 31.8 mmol, 1.00 equiv), Et$_3$N (9.65 g, 95.4 mmol, 3.00 equiv), and 50 w % T3P® in ethyl acetate (30.43 g, 47.8 mmol, 1.50 equiv) in that order. The reaction was stirred at 15-25° C. for 18 h. The mixture was diluted with ethyl acetate (450 mL, 10.0 mL/g) then washed with saturated Na$_2$CO$_3$ (450 mL, 10.0 mL/g). The organic layer was concentrated. The residue was purified by flash chromatography on silica gel and eluted with a mixture of PE/EA (5/1) to afford the product as a light yellow oil (2.64 g, 34.7%): $^1$H NMR (400 MHz, chloroform-d) δ 7.45 (d, J=12.0 Hz, 1H), 7.33-7.24 (m, 2H), 7.10-7.01 (m, 2H), 5.04 (d, J=12.0 Hz, 1H), 3.69 (q, J=7.1 Hz, 2H), 3.28-3.16 (m, 3H), 1.17 (t, J=7.0 Hz, 3H). $^{13}$C NMR (100 MHz, chloroform-d): 161.2, 142.9, 133.3, 129.9, 129.0, 97.4, 67.6, 37.3, 14.8. HRMS cacld for $C_{12}H_{15}ClNO_2$ [M+H]$^+$: 240.0791; found: 240.0794.

Example 19: (E)-3-Ethoxy-N-methyl-N-(o-tolyl)acrylamide (29)

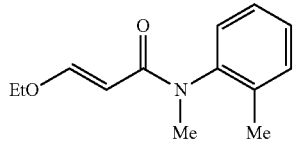

29

To a mixture of 3-ethoxyprop-2-enoic acid (4.79 g, 41.2 mmol, 1.00 equiv) and DMF (3.02 g, 41.3 mmol, 1.00 equiv) in DCM (50 mL, 10.4 mL/g) at rt was added oxalyl chloride (7.86 g, 61.9 mmol, 1.50 equiv) over 0.5 h. The mixture was aged at 15-25° C. for 3 h. The mixture was concentrated to dryness, dissolved in DCM (30 mL, 6.3 mL/g), then added drop-wise to a solution of N, methyl-o-toluidine (5.00 g, 41.3 mmol, 1.0 equiv), Et$_3$N (10.44 g, 103.2 mmol, 2.5 equiv), and DCM (30 mL, 6.3 mL/g). The reaction was stirred at 15-25° C. for 1 h. The reaction was quenched with H$_2$O (50 mL, 10.4 mL/g), extracted with three portions of DCM (50 mL, 10.4 mL/g), washed with three portions of H$_2$O (100 mL, 20.8 mL/g), then finally washed with brine (100 mL, 10.4 mL/g). The organic layer was concentrated. The residue was purified by flash chromatography on silica gel then eluted with a mixture of petroleum ether/EtOAc (6/1) to afford the product as a light yellow oil (5.79 g, 64%): $^1$H NMR (400 MHz, chloroform-d) δ 7.45 (d, J=12.0 Hz, 1H), 7.23-7.11 (m, 3H), 7.08-7.00 (m, 1H), 4.87 (d, J=12.2 Hz, 1H), 3.65 (q, J=7.1 Hz, 2H), 3.14 (s, 3H), 2.13 (s, 3H), 1.14 (t, J=7.1 Hz, 3H). $^{13}$C NMR (100 MHz, chloroform-d): 167.3, 160.7, 142.5, 136.0, 131.3, 128.4, 128.2, 127.3, 97.0, 67.3, 35.7, 17.5, 14.6. HRMS cacld for C$_{13}$H$_{18}$O$_2$N [M+H]$^+$: 220.1338; found: 220.1337.

Example 20: (E)-N,N-Dibenzyl-3-ethoxyacrylamide (30)

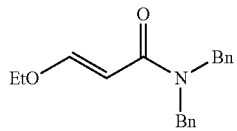

To a solution of N-benzyl-1-phenyl-methanamine (4.99 g, 25.3 mmol, 1.00 equiv) in DMF (50 mL, 10.0 mL/g) at rt was added (E)-3-ethoxyprop-2-enoic acid (3.24 g, 27.9 mmol, 1.10 equiv), Et$_3$N (3.9 mL, 28.0 mmol, 1.10 equiv), and TBTU (9.0 g, 27.9 mmol, 1.10 equiv) in that order. After 2 h at rt, H$_2$O (400 mL, 80.0 mL/g) and MTBE (400 mL, 80.0 mL/g) were added into the mixture. The organic layer was then separated and concentrated. The residue was purified by flash chromatography on silica gel then eluted with DCM to afford the product as a light yellow oil (1.58 g, 21%): $^1$H NMR (400 MHz, chloroform-d) δ 7.65 (d, J=11.7 Hz, 1H), 7.36-6.98 (m, 10H), 5.59 (d, J=11.7 Hz, 1H), 4.73-4.27 (m, 4H), 3.82 (q, J=7.1 Hz, 2H), 1.23 (t, J=7.0 Hz, 3H). $^{13}$C NMR (100 MHz, chloroform-d): 167.8, 162.1, 128.5, 128.3, 128.2, 127.9, 127.1, 126.9, 126.2, 119.6, 95.4, 67.2, 49.7, 48.1, 14.3. HRMS calcd for C$_{19}$H$_{22}$O$_2$N [M+H]$^+$: 296.1651; found: 296.1652.

Example 21: (E)-N-Benzyl-3-ethoxyacrylamide (31)

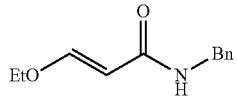

To a 400 mL reactor equipped with overhead agitation and under active nitrogen line at rt was combined (E)-3-ethoxy-prop-2-enoic acid (3.48 g, 30.0 mmol, 1.30 equiv), benzylamine (2.47 g, 23.0 mmol, 1.00 equiv), 2-PrOH (12.5 mL, 5.0 mL/g), Et$_3$N (13.0 mL, 93.0 mmol, 4.00 equiv), then 50 w % T3P® in ethyl acetate (17.0 mL, 28.0 mmol, 1.20 equiv) in that order (caution: exothermic temperature increase). The reaction was heated to 40° C. for 1 h then quenched with distilled water (37.5 mL, 15.0 mL/g). The layers were separated, the aqueous layer was extracted twice with DCM (25.0 mL, 10 mL/g), and then the organic layers were combined. The combined organic layer was then dried over sodium sulfate, filtered, then concentrated under reduced pressure. The crude residue was purified by flash chromatography on silica gel, eluted with a 25-50% IPAc: heptane gradient mobile phase, then concentrated to give the product as a white solid (61%): m.p. 67-68° C. FTIR (neat cm$^{-1}$) 3284, 2984, 1655, 1599, 1584, 1204, 1185, 849, 811, 602, 521. $^1$H NMR (400 MHz, DMSO-d$_6$) δ 8.12 (t, J=6.0 Hz, 1H), 7.37 (d, J=12.4 Hz, 1H), 7.34-7.28 (m, 2H), 7.27-7.22 (m, 3H), 5.40 (d, J=12.4 Hz, 1H), 4.31 (d, J=6.0 Hz, 2H), 3.87 (q, J=7.0 Hz, 2H), 1.24 (t, J=7.0 Hz, 3H). $^{13}$C NMR (101 MHz, DMSO-d$_6$) δ 165.8, 158.1, 139.8, 128.2, 127.3, 126.7, 99.4, 66.1, 41.9, 14.5. LRMS: calcd for C$_{12}$H$_{16}$NO$_2$ [M+H]$^+$: 206.1; found: 206.1.

Examples 22-36 illustrate procedures for the synthesis of various benzo[4,5]imidazo[1,2-a]pyrimidine-2-amines.

Example 22: General Procedure for the Synthesis of Benzo[4,5]imidazo[1,2-a]pyrimidin-2-amines To a dram vial containing a stir bar was added: acrylamide (1.00 mmol, 1.00 equiv), N-diethoxyphosphoryl-1H-benzimidazol-2-amine (0.296 g, 1.10 mmol, 1.10 equiv), followed by 2-methyltetrahydrofuran (1.0 mL, 1.0 mL/mmol) and acetonitrile (1.0 mL, 1.0 mL/mmol). The reaction was then cooled to 0° C. and phosphoryl chloride (0.204 mL, 2.20 mmol, 2.2 equiv) was added in one portion and then the reaction was placed in a 70° C. heating block. The reaction was allowed to stir at this temperature for 3 hours. After 3 hours at 70° C. the reaction was cooled to rt and quenched with Et$_3$N (1.0 mL). The mixture was then dry loaded onto silica gel and purified via automated silica gel column chromatography.

Example 23: 2-(4-Phenylpiperidin-1-yl)benzo[4,5]imidazo[1,2-a]pyrimidine (6a)

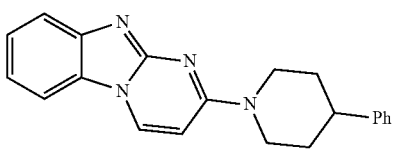

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.259 g, 1.00 mmol, 1.00 equiv) and N-diethoxyphosphoryl-1H-benzimidazol-2-amine (0.296 g, 1.10 mmol, 1.10 equiv) to yield compound 6a (0.312 g, 95%) as a white solid. Eluent gradient: 0-10% CH$_3$OH in CH$_2$Cl$_2$. m.p. 241-243° C.; FTIR (neat cm$^{-1}$) 1646, 1606, 1473, 1449, 1195, 738, 662; $^1$H NMR (400 MHz, chloroform-d) δ 8.23 (d, J=7.7 Hz, 1H), 7.73 (d, J=8.1 Hz, 1H), 7.55 (d, J=8.0 Hz, 1H), 7.37 (t, J=7.7 Hz, 1H), 7.31 (t, J=7.5 Hz, 2H), 7.26-7.14 (m, 4H), 6.44 (d, J=7.8 Hz, 1H), 4.77 (s, 2H), 3.09 (t, J=13.0 Hz, 2H), 2.85 (tt, J=12.2, 3.8 Hz, 1H), 2.00 (q, J=12.3 Hz, 2H), 1.75 (qd, J=12.8, 4.2 Hz, 2H). $^{13}$C NMR (101 MHz, chloroform-d) δ 157.9, 152.9, 145.2, 144.9, 132.7, 128.7, 127.9, 126.9, 126.9, 124.8, 119.8, 118.7, 108.8, 95.5, 45.8, 43.0, 33.3. HRMS: calcd for C$_{21}$H$_{21}$N$_4$ [M+H]$^+$: 329.1761; found: 329.1759.

Example 24: N-Methyl-N-phenylbenzo[4,5]imidazo[1,2-a]pyrimidin-2-amine (7a)

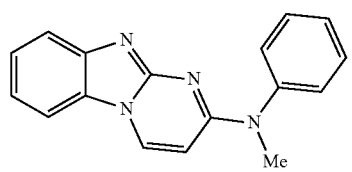

7a

General procedure for the synthesis of benzo[4,5]imidazo[1,2-a]pyrimidin-2-amines was performed with (E)-3-ethoxy-N-methyl-N-phenylacrylamide (0.103 g, 0.500 mmol, 1.00 equiv) and N-diethoxyphosphoryl-1H-benzimidazol-2-amine (0.148 g, 0.550 mmol, 1.10 equiv) to yield compound 7a (0.137 g, 87%) as a white solid. Eluent gradient: 0-10% CH$_3$OH in CH$_2$Cl$_2$. m.p. 270-271° C.; FTIR (neat cm$^{-1}$) 1640, 1588, 1504, 1449, 1366, 1247, 1366, 1247, 1222, 1121, 762, 702; $^1$H NMR (400 MHz, chloroform-d) δ 8.08 (d, J=7.6 Hz, 1H), 7.76 (d, J=8.1 Hz, 1H), 7.54 (d, J=8.0 Hz, 1H), 7.49 (t, J=7.6 Hz, 2H), 7.38 (t, J=7.5 Hz, 2H), 7.29 (d, J=7.5 Hz, 2H), 7.19 (t, J=7.6 Hz, 1H), 3.63 (s, 3H). $^{13}$C NMR (101 MHz, chloroform-d) δ 158.8, 144.8, 144.5, 131.7, 130.3, 127.9, 127.8, 127.3, 124.9, 120.1, 119.0, 108.9, 97.9, 39.1. HRMS: calcd for C$_{17}$H$_{15}$N$_4$ [M+H]$^+$: 275.1291; found: 275.1292.

Example 25: N-(4-Methoxyphenyl)-N-methylbenzo[4,5]imidazo[1,2-a]pyrimidin-2-amine (8a)

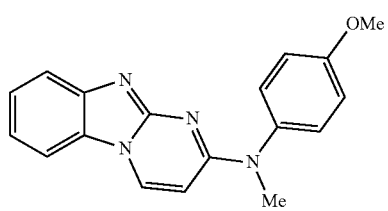

8a

General procedure for the synthesis of benzo[4,5]imidazo[1,2-a]pyrimidin-2-amines was performed with (E)-3-ethoxy-N-(4-methoxyphenyl)-N-methylacrylamide (0.118 g, 0.500 mmol, 1.00 equiv) and N-diethoxyphosphoryl-1H-benzimidazol-2-amine (0.148 g, 0.550 mmol, 1.10 equiv) to yield compound 8a (0.152 g, 92%) as a white solid. Eluent gradient: 0-10% CH$_3$OH in CH$_2$Cl$_2$. m.p. 287-289° C.; FTIR (neat cm$^{-1}$) 1644, 1609, 1507, 1438, 1369, 1264, 1023, 789, 736; $^1$H NMR (400 MHz, chloroform-d) δ 8.05 (d, J=6.4 Hz, 1H), 7.75 (d, J=8.1 Hz, 2H), 7.53 (d, J=8.0 Hz, 2H), 7.37 (s, 1H), 7.19 (dt, J=8.7, 1.7 Hz, 5H), 6.99 (d, J=7.3 Hz, 3H), 6.03 (dd, J=7.7, 1.3 Hz, 2H), 3.86 (s, 3H), 3.58 (s, 3H). $^{13}$C NMR (101 MHz, chloroform-d) δ 159.2, 159.0, 152.8, 144.8, 137.2, 131.6, 128.6, 127.9, 124.8, 120.0, 118.9, 115.5, 108.8, 97.8, 55.7, 39.2. HRMS: calcd for C$_{18}$H$_{17}$N$_4$O [M+H]$^+$: 305.1397; found: 305.1398.

Example 26: N-Methyl-N-(4-(trifluoromethyl)phenyl)benzo[4,5]imidazo[1,2-a]pyrimidin-2-amine (9a)

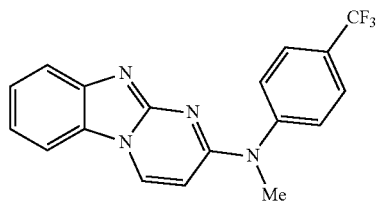

9a

General procedure for the synthesis of benzo[4,5]imidazo[1,2-a]pyrimidin-2-amines was performed with (E)-3-ethoxy-N-methyl-N-(4-(trifluoromethyl)phenyl)acrylamide (0.137 g, 0.500 mmol, 1.00 equiv) and N-diethoxyphosphoryl-1H-benzimidazol-2-amine (0.148 g, 0.550 mmol, 1.10 equiv) to yield compound 9a (0.142 g, 83%) as a white solid. Eluent gradient: 0-10% CH$_3$OH in CH$_2$Cl$_2$. m.p. 271-273° C.; FTIR (neat cm$^{-1}$) 1654, 1608, 1458, 1319, 1122, 1103, 1059, 765, 737; $^1$H NMR (400 MHz, chloroform-d) δ 8.17 (d, J=7.7 Hz, 1H), 7.77 (dd, J=14.6, 8.1 Hz, 3H), 7.59 (d, J=8.1 Hz, 1H), 7.42 (dd, J=17.4, 8.3 Hz, 3H), 7.32-7.18 (m, 1H), 6.16 (d, J=7.6 Hz, 1H), 3.66 (s, 3H). $^{13}$C NMR (101 MHz, chloroform-d) δ 158.2, 144.6, 132.1, 127.7, 127.3, 127.3, 127.2, 125.0, 120.3, 119.1, 109.0, 97.5, 38.9. $^{19}$F NMR (376 MHz, chloroform-d) δ -62.50. HRMS: calcd for C$_{18}$H$_{14}$F$_3$N$_4$ [M+H]$^+$: 343.1165; found: 343.1166.

Example 27: N-(4-Chlorophenyl)-N-methylbenzo[4,5]imidazo[1,2-a]pyrimidin-2-amine (10a)

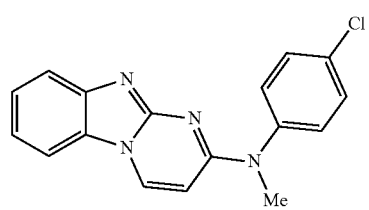

10a

General procedure for the synthesis of benzo[4,5]imidazo[1,2-a]pyrimidin-2-amines was performed with (E)-N-(4-chlorophenyl)-3-ethoxy-N-methylacrylamide (0.120 g, 0.500 mmol, 1.00 equiv) and N-diethoxyphosphoryl-1H-benzimidazol-2-amine (0.148 g, 0.550 mmol, 1.10 equiv) to yield compound 10a (0.139 g, 90%) as a white solid. Eluent gradient: 0-10% CH$_3$OH in CH$_2$Cl$_2$. m.p. 248-250° C.; FTIR (neat cm$^{-1}$) 1640, 1450, 1361, 810, 762, 733, 554, 430; $^1$H NMR (400 MHz, chloroform-d) δ 8.12 (d, J=7.6 Hz, 1H), 7.77 (d, J=8.1 Hz, 1H), 7.56 (d, J=8.0 Hz, 1H), 7.46 (d, J=8.3 Hz, 2H), 7.40 (t, J=7.7 Hz, 1H), 7.34-7.17 (m, 2H), 6.08 (d, J=7.6 Hz, 1H), 3.61 (s, 1H). $^{13}$C NMR (101 MHz, chloroform-d) δ 158.6, 144.8, 143.1, 133.4, 132.0, 130.5, 128.7, 127.9, 125.0, 120.3, 119.1, 109.0, 97.6, 39.1. HRMS: calcd for C$_{17}$H$_{14}$ClN$_4$ [M+H]$^+$: 309.0902; found: 309.0905.

Example 28: N-Methyl-N-(o-tolyl)benzo[4,5]imidazo[1,2-a]pyrimidin-2-amine (11a)

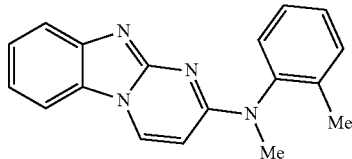

11a

General procedure for the synthesis of benzo[4,5]imidazo[1,2-a]pyrimidin-2-amines was performed with (E)-3-ethoxy-N-methyl-N-(o-tolyl)acrylamide (0.110 g, 0.500 mmol, 1.00 equiv) and N-diethoxyphosphoryl-1H-benzimidazol-2-amine (0.148 g, 0.550 mmol, 1.10 equiv) to yield compound 11a (0.112 g, 78%) as a white solid. Eluent gradient: 0-10% CH$_3$OH in CH$_2$Cl$_2$. m.p. 218-220° C.; FTIR (neat cm$^{-1}$) 1640, 1449, 1367, 1250, 1110, 776, 707; $^1$H NMR (400 MHz, chloroform-d) δ 8.06 (d, J=7.6 Hz, 1H), 7.75 (d, J=8.1 Hz, 1H), 7.53 (d, J=8.0 Hz, 1H), 7.41-7.27 (m, 4H), 7.24-7.14 (m, 2H), 5.77 (d, J=7.6 Hz, 1H), 3.55 (s, 3H), 2.19 (s, 3H). $^{13}$C NMR (101 MHz, chloroform-d) δ 158.8, 144.8, 142.7, 136.4, 132.0, 131.9, 128.7, 128.5, 128.1, 127.9, 124.8, 120.0, 118.9, 108.8, 97.3, 37.8, 17.6. HRMS: calcd for C$_{18}$H$_{17}$N$_4$ [M+H]$^+$: 289.1448; found: 289.1443.

Example 29: N,N-Dibenzylbenzo[4,5]imidazo[1,2-a]pyrimidin-2-amine (12a)

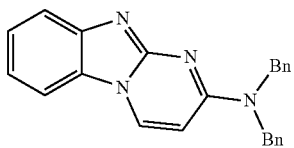

12a

General procedure for the synthesis of benzo[4,5]imidazo[1,2-a]pyrimidin-2-amines was performed with (E)-N,N-dibenzyl-3-ethoxyacrylamide (0.148 g, 0.500 mmol, 1.00 equiv) and N-diethoxyphosphoryl-1H-benzimidazol-2-amine (0.148 g, 0.550 mmol, 1.10 equiv) to yield compound 12a (0.163 g, 89%) as a white solid. Eluent gradient: 0-10% CH$_3$OH in CH$_2$Cl$_2$. m.p. 189-191° C.; FTIR (neat cm$^{-1}$) 1640, 1583, 1478, 1443, 1218, 927, 734, 720, 691; $^1$H NMR (400 MHz, chloroform-d) δ 8.21 (d, J=7.6 Hz, 1H), 7.76 (d, J=8.1 Hz, 1H), 7.54 (d, J=8.0 Hz, 1H), 7.42-7.23 (m, 11H), 7.19 (t, J=7.6 Hz, 1H), 6.29 (d, J=7.7 Hz, 1H), 5.09-4.69 (bs, 4H). $^{13}$C NMR (101 MHz, chloroform-d) δ 159.1, 144.9, 133.0, 129.0, 127.8, 127.8, 125.0, 120.0, 118.9, 110.1, 108.9, 96.0, 51.1. HRMS: calcd for C$_{24}$H$_{21}$N$_4$ [M+H]$^+$: 365.1761; found: 365.1766.

Example 30: N-Benzylbenzo[4,5]imidazo[1,2-a]pyrimidin-2-amine (13a)

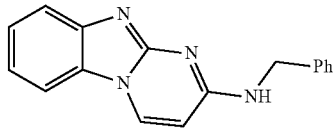

13a

General procedure for the synthesis of benzo[4,5]imidazo[1,2-a]pyrimidin-2-amines was performed with (E)-N-benzyl-3-ethoxyacrylamide (0.205 g, 1.00 mmol, 1.00 equiv) and N-diethoxyphosphoryl-1H-benzimidazol-2-amine (0.296 g, 1.10 mmol, 1.10 equiv) to yield compound 13a (0.175 g, 64%) as a white solid. Eluent gradient: 0-10% CH$_3$OH in CH$_2$Cl$_2$. m.p. 270-272° C.; FTIR (neat cm$^{-1}$) 1644, 1585, 1493, 1444, 1340, 1320, 1039, 794, 729; $^1$H NMR (400 MHz, DMSO-d$_6$) δ 8.82 (d, J=7.4 Hz, 1H), 8.39 (t, J=5.8 Hz, 1H), 7.88 (d, J=7.9 Hz, 1H), 7.50 (d, J=8.0 Hz, 1H), 7.44-7.31 (m, 4H), 7.31-7.23 (m, 2H), 7.15 (t, J=7.6 Hz, 1H), 6.43 (d, J=7.3 Hz, 1H), 4.65 (d, J=5.6 Hz, 2H). $^{13}$C NMR (101 MHz, DMSO-d$_6$) δ 158.8, 152.4, 143.8, 139.0, 133.3, 128.4, 128.0, 127.6, 127.0, 123.9, 119.2, 117.2, 109.9, 99.2, 43.6. HRMS: calcd for C$_{17}$H$_{15}$N$_4$ [M+H]$^+$: 275.1291; found: 275.1277.

Example 31: 8-Methoxy-2-(4-phenylpiperidin-1-yl)benzo[4,5]imidazo[1,2-a]pyrimidine (14a)

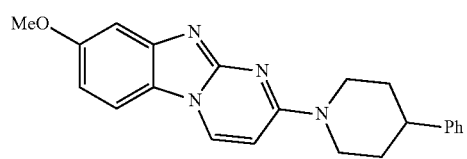

14a

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.259 g, 1.00 mmol, 1.00 equiv) and diethyl (Z)-(5-methoxy-1,3-dihydro-2H-benzo[d]imidazol-2-ylidene)phosphoramidate (0.329 g, 1.10 mmol, 1.1 equiv) to yield a mixture of 14a and 14a' as a yellow solid (0.342 g, 95%, 55:45 14a:14a'). Eluent gradient: 0-10% CH$_3$OH in CH$_2$Cl$_2$. This mixture of isomers was then subjected to SFC purification (cellulose 3 column, eluent: 25% MeOH-isocratic) to provide an analytically pure sample of 14a. m.p. 248-250° C.; FTIR (neat, cm$^{-1}$) 1666, 1503, 1477, 1281, 1210, 1172, 775, 753, 699; $^1$H NMR (400 MHz, acetic acid-d$_4$) δ 8.79 (d, J=7.6 Hz, 1H), 7.84 (d, J=8.9 Hz, 1H), 7.36-7.15 (m, 6H), 7.12 (d, J=7.7 Hz, 1H), 7.00 (dd, J=9.0, 2.3 Hz, 1H), 5.22 (d, J=13.1 Hz, 1H), 4.66-4.28 (m, 1H), 3.88 (s, 3H), 3.46 (t, J=13.2 Hz, 1H), 3.15 (t, J=12.8 Hz, 1H), 2.99 (tt, J=12.1, 3.6 Hz, 1H), 2.08 (q, J=11.6, 10.2 Hz, 2H), 1.93-1.65 (m, 2H). $^{13}$C NMR (101 MHz, acetic acid-d$_4$) δ 160.6, 159.7, 148.6, 145.8, 135.6, 132.3, 129.6, 127.6, 127.5, 120.4, 113.4, 112.8, 100.7, 97.8, 56.5, 48.2, 46.1, 43.0, 34.2, 33.6. HRMS: calcd for C$_{22}$H$_{23}$N$_4$O$^+$ [M+H]$^+$: 359.1866; found: 359.1867.

Example 32: 7-Methoxy-2-(4-phenylpiperidin-1-yl)benzo[4,5]imidazo[1,2-a]pyrimidine (14a')

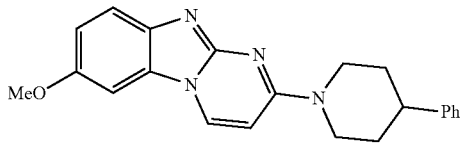

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.259 g, 1.00 mmol, 1.00 equiv) and diethyl (Z)-(5-methoxy-1,3-dihydro-2H-benzo[d]imidazol-2-ylidene)phosphoramidate (0.329 g, 1.10 mmol, 1.10 equiv) to yield a mixture of 14a and 14a' as a yellow solid (0.342 g, 95%, 55:45 14a:14a'). Eluent gradient: 0-10% $CH_3OH$ in $CH_2Cl_2$. This mixture of isomers was then subjected to SFC purification (cellulose 3 column, eluent: 25% MeOH-isocratic) to provide an analytically pure sample of 14a'. m.p. 202-205° C.; FTIR (neat, cm$^{-1}$) 1638, 1477, 1443, 1281, 1210, 1172, 775, 753, 699; $^1$H NMR (400 MHz, DMSO-d$_6$) δ 8.92 (d, J=7.8 Hz, 1H), 7.65 (d, J=2.5 Hz, 1H), 7.42 (d, J=8.7 Hz, 1H), 7.36-7.12 (m, 5H), 6.98-6.64 (m, 2H), 4.72 (s, 2H), 3.82 (s, 3H), 3.08 (t, J=12.7 Hz, 2H), 2.89 (tt, J=12.2, 3.6 Hz, 1H), 2.03-1.80 (m, 2H), 1.63 (qd, J=12.6, 4.0 Hz, 2H). $^{13}$C NMR (101 MHz, DMSO-d$_6$) δ 157.4, 153.7, 151.5, 145.6, 138.2, 134.1, 128.4, 128.0, 126.7, 126.2, 117.7, 112.9, 109.5, 95.8, 94.9, 55.7, 44.9, 41.9, 32.8. HRMS: calcd for $C_{22}H_{23}N_4O^+$ [M+H]$^+$: 359.1866; found: 359.1867.

Example 33: 9-Bromo-2-(4-phenylpiperidin-1-yl)benzo[4,5]imidazo[1,2-a]pyrimidine (15a)

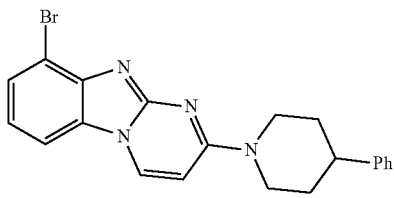

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.259 g, 1.00 mmol, 1.00 equiv) and diethyl (Z)-(4-bromo-1,3-dihydro-2H-benzo[d]imidazol-2-ylidene)phosphoramidate (0.383 g, 1.10 mmol, 1.10 equiv) to yield compound 15a (0.407 g, 77%) as a yellow solid. Eluent gradient: 0-10% $CH_3OH$ in $CH_2Cl_2$. m.p. 196-198° C.; FTIR (neat cm$^{-1}$) 1638, 1476, 1423, 1221, 765, 735, 684; $^1$H NMR (400 MHz, chloroform-d) δ 8.16 (d, J=7.7 Hz, 1H), 7.52 (d, J=7.8 Hz, 1H), 7.43 (d, J=7.9 Hz, 1H), 7.34-7.25 (m, 2H), 7.24-7.15 (m, 3H), 7.00 (t, J=7.9 Hz, 1H), 6.44 (d, J=7.8 Hz, 1H), 4.74 (s, 2H), 3.18-2.96 (m, 2H), 2.84 (tt, J=12.1, 3.7 Hz, 1H), 2.04-1.92 (m, 2H), 1.72 (qd, J=12.7, 4.2 Hz, 2H). $^{13}$C NMR (101 MHz, chloroform-d) δ 157.9, 152.8, 145.0, 143.4, 132.8, 128.7, 128.1, 127.6, 126.8, 126.6, 120.4, 111.6, 108.0, 96.2, 45.8, 42.8, 33.2. HRMS: calcd for $C_{21}H_{20}BrN_4$ [M+H]$^+$: 407.0866; found: 407.0845.

Example 34: tert-Butyl 2-(4-phenylpiperidin-1-yl)benzo[4,5]imidazo[1,2-a]pyrimidine-9-carboxylate (16a)

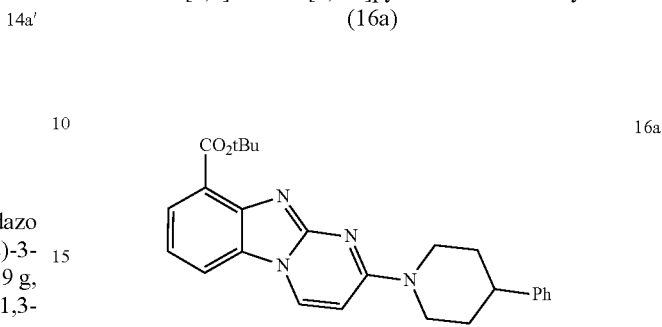

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.065 g, 0.250 mmol, 1.00 equiv) and tert-butyl (Z)-2-((diethoxyphosphoryl)imino)-2,3-dihydro-1H-benzo[d]imidazole-4-carboxylate (0.102 g, 0.275 mmol, 1.10 equiv) to yield compound 16a (0.089 g, 83%) as a white solid. Eluent gradient: 0-10% $CH_3OH$ in $CH_2Cl_2$. m.p. 197-199° C.; FTIR (neat cm$^{-1}$) 1683, 1633, 1459, 1222, 1132, 1006, 702; $^1$H NMR (400 MHz, chloroform-d) δ 8.37 (d, J=7.7 Hz, 1H), 7.95 (dd, J=7.8, 1.1 Hz, 1H), 7.73 (dd, J=7.9, 1.1 Hz, 1H), 7.31 (ddt, J=7.2, 6.5, 0.9 Hz, 2H), 7.25-7.14 (m, 4H), 6.52 (d, J=7.8 Hz, 1H), 4.78 (s, 2H), 3.10 (t, J=13.3 Hz, 2H), 2.85 (tt, J=12.2, 3.7 Hz, 1H), 2.08-1.93 (m, 2H), 1.81-1.71 (m, 2H), 1.67 (s, 9H). $^{13}$C NMR (101 MHz, chloroform-d) δ 165.0, 158.2, 153.8, 145.1, 144.1, 132.9, 129.1, 128.7, 127.1, 126.9, 126.7, 121.4, 118.7, 112.5, 96.3, 80.9, 42.9, 33.3, 28.5. HRMS: calcd for $C_{26}H_{29}N_4O_2$ [M+H]$^+$: 429.2285; found: 429.2286.

Example 35: 7-(4-Phenylpiperidin-1-yl)imidazo[1,2-a]pyrimidine (17a)

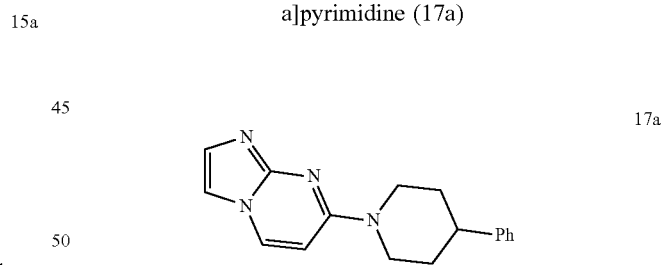

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.259 g, 1.00 mmol, 1.00 equiv) and diethyl (1,3-dihydro-2H-imidazol-2-ylidene)phosphoramidate (0.241 g, 1.10 mmol, 1.10 equiv) to yield compound 17a (0.215 g, 77%) as an off-white solid. Eluent gradient: 0-10% $CH_3OH$ in $CH_2Cl_2$. m.p. 190-193° C.; FTIR (neat cm$^{-1}$) 1643, 1542, 1515, 1477, 1219, 1008; $^1$H NMR (400 MHz, chloroform-d) δ 8.02 (d, J=7.7 Hz, 1H), 7.37 (d, J=1.6 Hz, 1H), 7.34-7.24 (m, 2H), 7.20 (ddd, J=7.8, 5.9, 1.7 Hz, 3H), 7.13 (d, J=1.6 Hz, 1H), 4.64 (d, J=13.4 Hz, 1H), 3.03 (td, J=13.3, 2.6 Hz, 2H), 2.80 (tt, J=12.2, 3.7 Hz, 1H), 1.95 (d, J=12.8 Hz, 2H), 1.72 (qd, J=12.7, 4.1 Hz, 2H). $^{13}$C NMR (101 MHz, chloroform-d) δ 156.2, 149.9, 145.4, 133.7, 132.5, 128.6, 126.8, 126.5, 108.8, 97.5, 45.8, 43.0, 33.1. HRMS: calcd for $C_{17}H_{19}N_4$ [M+H]$^+$: 279.1604; found: 279.1599.

Example 36: Ethyl 7-(4-phenylpiperidin-1-yl)imidazo[1,2-a]pyrimidine-2-carboxylate (18a)

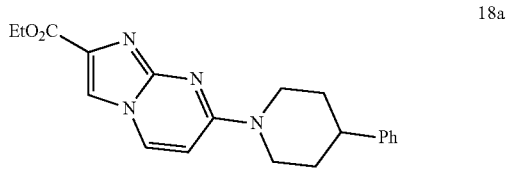 [SMILES: CCOC(=O)c1cn2ccc(N3CCC(c4ccccc4)CC3)nc2n1]

18a

General procedure for the synthesis of benzo[4,5]imidazo[1,2-a]pyrimidin-2-amines was performed with (E)-3-ethoxy-1-(4-phenylpiperidin-1-yl)prop-2-en-1-one (0.130 g, 0.500 mmol, 1.00 equiv) and ethyl (Z)-2-((diethoxyphosphoryl)imino)-2,3-dihydro-1H-imidazole-4-carboxylate (0.160 g, 0.550 mmol, 1.10 equiv) to yield compound 18a (0.152 g, 87%) as a white solid. Eluent gradient: 0-10% CH$_3$OH in CH$_2$Cl$_2$. m.p. 205-207° C.; FTIR (neat cm$^{-1}$) 1715, 1650, 1519, 1492, 1208, 1183, 1120, 752; $^1$H NMR (400 MHz, chloroform-d) δ 8.02 (d, J=7.8 Hz, 1H), 7.77 (s, 1H), 7.35-7.25 (m, 3H), 7.25-7.15 (m, 3H), 6.55 (d, J=7.8 Hz, 1H), 4.66 (d, J=13.1 Hz, 2H), 4.39 (q, J=7.1 Hz, 2H), 3.07 (td, J=13.2, 2.5 Hz, 2H), 2.83 (tt, J=12.2, 3.7 Hz, 1H), 2.02-1.90 (m, 2H), 1.73 (dtd, J=13.4, 12.4, 4.2 Hz, 3H), 1.40 (t, J=7.1 Hz, 3H). $^{13}$C NMR (101 MHz, chloroform-d) δ 163.8, 156.6, 149.5, 145.3, 135.9, 133.8, 128.7, 126.9, 126.7, 114.0, 99.4, 60.9, 45.9, 43.0, 33.1, 14.5. HRMS: calcd for $C_{20}H_{23}N_4O_2$ [M+H]$^+$: 351.1816; found: 351.1815.

Examples 37-42 illustrate procedures for the synthesis of various benzo[4,5]imidazo[1,2-a]pyrimidine-4-amines

Example 37: General Procedure for the Synthesis of Benzo[4,5]imidazo[1,2-a]pyrimidin-4-amines To a dram vial containing a stir bar was added acrylamide (0.50 mmol, 1.0 equiv) followed by 2-methyltetrahydrofuran (1.0 mL, 1.0 mL/mmol) and acetonitrile (1.0 mL, 1.0 mL/mmol). Then the reaction was cooled to 0° C. and phosphoryl chloride (56 µL, 0.60 mmol, 1.2 equiv) was added in one portion. The reaction mixture was then heated to 80° C. for 15 minutes and then allowed to cool to rt. At this time the cap was removed from the dram vial and 1-diethoxyphosphorylbenzimidazol-2-amine (0.404 g, 1.5 mmol, 3.0 equiv) was added to the reaction mixture. The cap was replaced and the reaction was then placed in a 50° C. heating block and allowed to react for 3 h. After 3 h the reaction mixture was allowed to cool to rt and was then quenched with Et$_3$N (1.0 mL). The mixture was then dry loaded onto silica gel and purified via automated silica gel column chromatography.

Example 38: 4-(4-Phenylpiperidin-1-yl)benzo[4,5]imidazo[1,2-a]pyrimidine (6b)

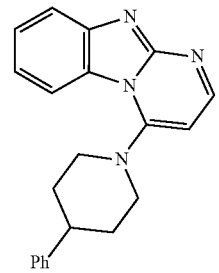

6b

General procedure for the synthesis of benzo[4,5]imidazo[1,2-a]pyrimidin-4-amines was performed with (E)-3-ethoxy-1-(4-phenylpiperidin-1-yl)prop-2-en-1-one (0.130 g, 0.500 mmol, 1.00 equiv) to yield compound 6b (0.146 g, 89%) as a light yellow solid. Eluent gradient: 0-10% CH$_3$OH in CH$_2$Cl$_2$. m.p. 203-204° C.; FTIR (neat cm$^{-1}$) 1584, 1505, 1429, 1177, 761, 740, 703; $^1$H NMR (400 MHz, chloroform-d) δ 8.64 (d, J=4.8 Hz, 1H), 8.16 (d, J=8.3 Hz, 1H), 8.00 (d, J=8.2 Hz, 1H), 7.56 (t, J=7.7 Hz, 1H), 7.45-7.24 (m, 6H), 6.42 (d, J=4.8 Hz, 1H), 3.76 (d, J=11.8 Hz, 2H), 2.88 (dtd, J=28.1, 11.0, 10.6, 5.0 Hz, 3H), 2.18 (td, J=10.3, 9.5, 3.6 Hz, 4H). $^{13}$C NMR (101 MHz, chloroform-d) δ 157.3, 155.9, 144.7, 144.6, 128.9, 127.1, 127.0, 126.8, 126.0, 121.2, 120.1, 115.2, 110.1, 95.0, 50.9, 42.0, 32.6. HRMS: calcd for $C_{21}H_{21}N_4$ [M+H]$^+$: 329.1761; found: 329.1762.

Example 39: N-methyl-N-phenylbenzo[4,5]imidazo[1,2-a]pyrimidin-4-amine (7b)

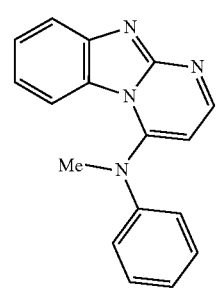

7b

General procedure for the synthesis of benzo[4,5]imidazo[1,2-a]pyrimidin-4-amines was performed with (E)-3-ethoxy-N-methyl-N-phenylacrylamide (0.103 g, 0.500 mmol, 1.00 equiv) to yield compound 7b (0.122 g, 89%) as a yellow solid. Eluent gradient: 0-10% CH$_3$OH in CH$_2$Cl$_2$. m.p. 165-175° C.; FTIR (neat cm$^{-1}$) 1589, 1470, 1443, 1368, 755, 723, 690; $^1$H NMR (400 MHz, chloroform-d) δ 8.70 (d, J=4.7 Hz, 1H), 7.96 (d, J=8.7 Hz, 1H), 7.69 (d, J=8.5 Hz, 1H), 7.47 (t, J=7.7 Hz, 1H), 7.28 (t, J=7.3 Hz, 2H), 7.16 (t, J=7.8 Hz, 1H), 7.06 (t, J=7.4 Hz, 1H), 6.92 (d, J=8.9 Hz, 2H), 6.60 (dd, J=4.7, 1.1 Hz, 1H), 3.50 (s, 3H). $^{13}$C NMR (101 MHz, chloroform-d) δ 155.7, 153.3, 145.3, 144.6, 129.9, 127.3, 126.4, 126.2, 123.8, 121.5, 119.9, 118.7, 115.7, 100.7, 40.0. HRMS: calcd for $C_{17}H_{15}N_4$ [M+H]$^+$: 275.1291; found: 275.1288.

Example 40: N-(4-Methoxyphenyl)-N-methylbenzo[4,5]imidazo[1,2-a]pyrimidin-4-amine (8b)

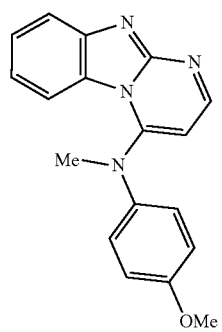

8b

General procedure for the synthesis of benzo[4,5]imidazo[1,2-a]pyrimidin-4-amines was performed with (E)-3-ethoxy-N-(4-methoxyphenyl)-N-methylacrylamide (0.118 g, 0.500 mmol, 1.00 equiv) to yield compound 8b (0.128 g, 84%) as a yellow-green solid. Eluent gradient: 0-10% CH$_3$OH in CH$_2$Cl$_2$. m.p. 176-177° C.; FTIR (neat cm$^{-1}$) 1593, 1494, 1445, 1371, 1238, 1030, 827, 726, 533; $^1$H NMR (400 MHz, chloroform-d) δ 8.65 (d, J=4.9 Hz, 1H), 7.94 (d, J=8.2 Hz, 1H), 7.74 (d, J=8.4 Hz, 1H), 7.51-7.42 (m, 1H), 7.20-7.11 (m, 1H), 6.90 (d, J=8.7 Hz, 1H), 6.81 (d, J=8.9 Hz, 2H), 6.50 (d, J=4.8 Hz, 1H), 3.74 (s, 2H), 3.47 (s, 2H). $^{13}$C NMR (101 MHz, chloroform-d) δ 156.7, 155.5, 154.0, 153.2, 144.6, 138.7, 126.5, 126.0, 121.5, 121.2, 119.8, 115.9, 115.2, 99.3, 55.6, 40.9. HRMS: calcd for C$_{18}$H$_{17}$N$_4$O [M+H]$^+$: 305.1397; found: 305.1395.

Example 41: N-(4-Chlorophenyl)-N-methylbenzo[4,5]imidazo[1,2-a]pyrimidin-4-amine (10b)

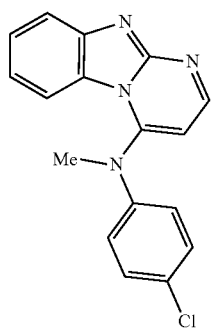

10b

General procedure for the synthesis of benzo[4,5]imidazo[1,2-a]pyrimidin-4-amines was performed with (E)-N-(4-chlorophenyl)-3-ethoxy-N-methylacrylamide (0.120 g, 0.500 mmol, 1.00 equiv) to yield compound 10b (0.101 g, 65%) as a yellow-green solid. Eluent gradient: 0-10% CH$_3$OH in CH$_2$Cl$_2$. m.p. 199-202° C.; FTIR (neat cm$^{-1}$) 1594, 1487, 1444, 1372, 1117, 813, 738; $^1$H NMR (400 MHz, chloroform-d) δ 8.70 (d, J=4.7 Hz, 1H), 7.97 (d, J=8.3 Hz, 1H), 7.67 (d, J=8.4 Hz, 1H), 7.50 (t, J=7.7 Hz, 1H), 7.27-7.15 (m, 3H), 6.84 (d, J=8.6 Hz, 2H), 6.60 (d, J=4.6 Hz, 1H), 3.48 (s, 3H). $^{13}$C NMR (101 MHz, chloroform-d) δ 155.7, 152.9, 152.8, 144.7, 144.0, 129.9, 129.0, 126.3, 126.2, 121.8, 120.2, 119.6, 115.5, 101.0, 39.9. HRMS: calcd. for C$_{17}$H$_{14}$ClN$_4$ [M+H]$^+$: 309.0902; found: 309.0888.

Example 42: N,N-Dibenzylbenzo[4,5]imidazo[1,2-a]pyrimidin-4-amine (12b)

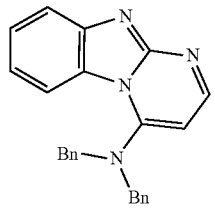

12b

General procedure for the synthesis of benzo[4,5]imidazo[1,2-a]pyrimidin-4-amines was performed with (E)-N,N-dibenzyl-3-ethoxyacrylamide (0.148 g, 0.500 mmol, 1.00 equiv) to yield compound 12b (0.146 g, 80%) as a yellow solid. Eluent gradient: 0-10% CH$_3$OH in CH$_2$Cl$_2$. m.p. 240-244° C.; FTIR (neat cm$^{-1}$) 1645, 1610, 1477, 1192, 1023, 947, 749; $^1$H NMR (400 MHz, chloroform-d) δ 8.54 (d, J=4.8 Hz, 1H), 8.25 (d, J=8.3 Hz, 1H), 8.06 (d, J=8.2 Hz, 1H), 7.61 (t, J=7.7 Hz, 1H), 7.45 (t, J=7.8 Hz, 1H), 7.40-7.30 (m, 6H), 7.09 (dd, J=6.5, 2.8 Hz, 4H), 6.11 (d, J=4.8 Hz, 1H), 4.45 (s, 2H), 4.31 (s, 2H). $^{13}$C NMR (101 MHz, chloroform-d) δ 155.2, 154.5, 153.5, 144.9, 134.5, 129.2, 128.9, 128.5, 127.2, 126.2, 121.6, 120.3, 115.6, 98.8, 53.9. HRMS: calcd for C$_{24}$H$_{21}$N$_4$ [M+H]$^+$: 365.1761; found: 365.1761.

Example 43: Computations

All calculations were performed using Gaussian 09 (Rev. E.01; available from Gaussian, Inc., Wallingford, Conn.). Terminology used in this example can be further understood by reference to documentation and user manuals that are distributed with Gaussian 09.

Density functional theory (DFT) computational analysis (level of theory: M062X/Def2TZVP, SMD(acetonitrile)) of the charge density of the nitrogen atoms in phosphoramidates 2a and 2b and in 2-aminobenzimidazole 1 indicated similar charge density and magnitude of charge across the relevant nitrogen atoms (FIG. 6), which suggests that selectivity in the reactions described herein is not solely governed by electronic factors. This suggests that the reaction proceeds via a 1,4-addition mechanism, as this would allow for a less sterically congested transition state during the initial C—N bond-forming event between 2a and 19.

To ensure the lowest energy structures were identified, conformational isomers and tautomers were exhaustively studied. All geometry optimizations were performed using B3LYP functional and Grimme dispersion correction D3BJ with 6-311G(d,p). Frequency calculations were performed at the same level of theory to obtain thermal corrections at 298 K. All minima were confirmed by having zero negative frequencies. Single point energy calculations were performed at the M062X level of theory with Def2-TZVP. Implicit solvation was applied using SMD=acetonitrile. Partial charges were calculated using the keyword pop=nbo. All final Gibbs free energies correspond to a standard state of 1 atm.

Figure 6:
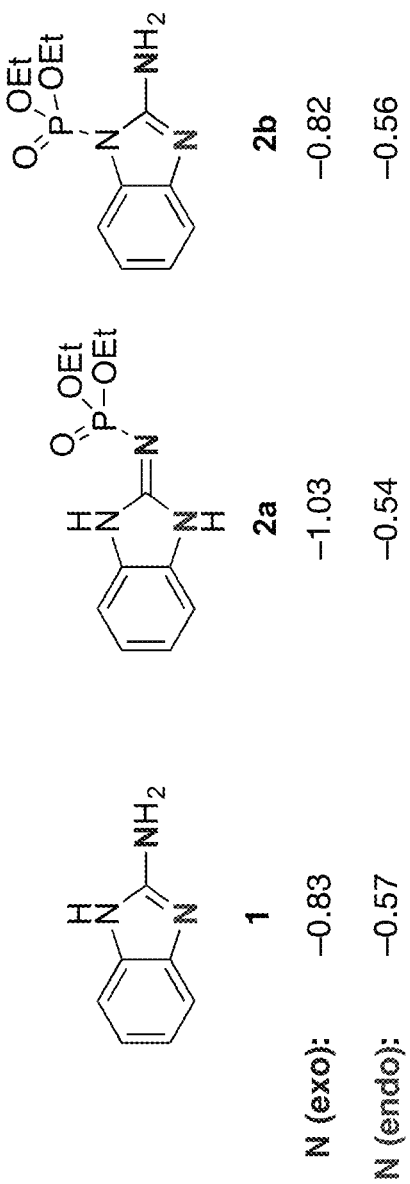
FIG. 6: Calculated partial charges of nitrogen atoms in amino-benzimidazole coupling partners.
Figure 7:
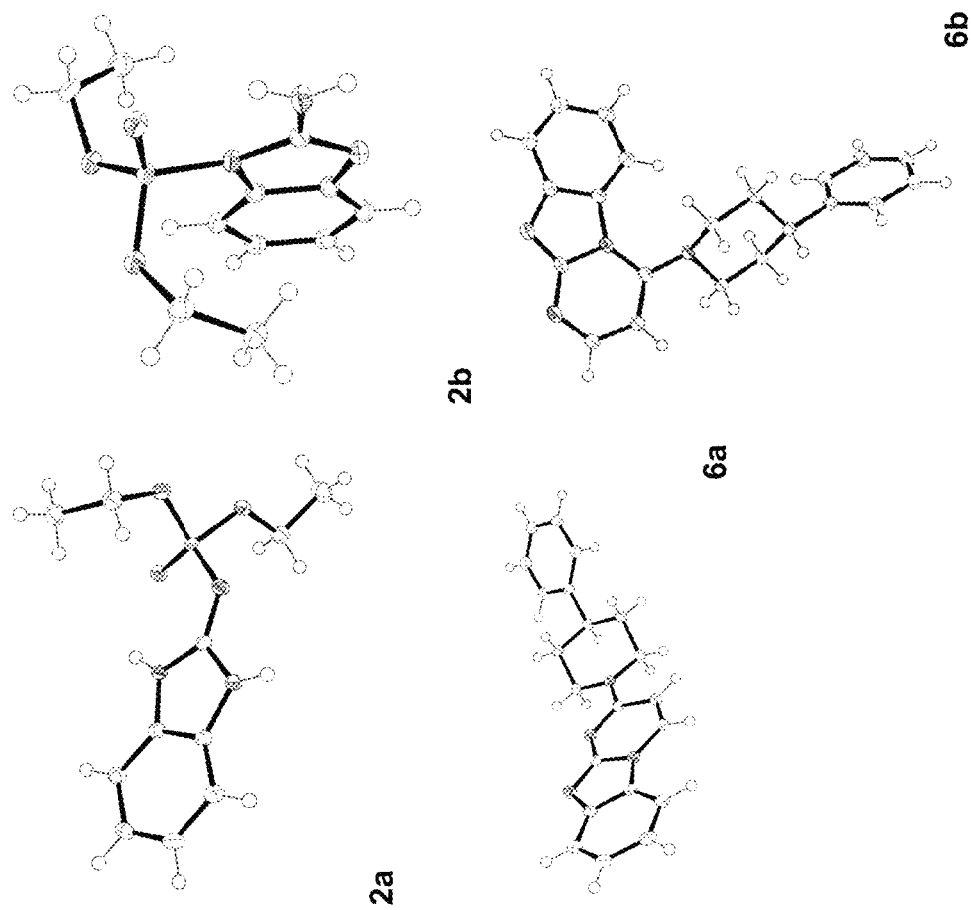
FIG. 7: X-ray crystallography structures of various compounds as described herein.

In FIG. 6, only the lowest energy structures of 1, 2a, and 2b are shown. These were calculated to be substantially lower in energy (>2.0 kcal/mol) relative to their tautomers and had nearly identical partial charges.

Examples 44-47 provide crystallography data for various molecules described elsewhere herein.

Example 44: X-Ray Analysis of 2a

X-ray quality crystals were used as received. The obtained crystal parameters are presented in Table 2. A colorless block 0.260×0.190×0.120 mm in size was mounted on a Cryoloop with Paratone oil. Data were collected in a nitrogen gas stream at 90(2) K using phi and omega scans. Crystal-to-detector distance was 40 mm and exposure time was 0.05 seconds per frame using a scan width of 0.5°. Data collection was 100.0% complete to 67.000° in θ. A total of 28327 reflections were collected covering the indices, $-12<=h<=12$, $-17<=k<=17$, $-11<=l<=11$. 2654 reflections were found to be symmetry independent, with an $R_{int}$ of 0.0402. Indexing and unit cell refinement indicated a primitive, monoclinic lattice. The space group was found to be P 21/c (No. 14). The data were integrated and scaled using CrysAlisPro 1.171.40.14e. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018.

Example 45: X-Ray Analysis of 2b

X-ray quality crystals were used as received. The obtained crystal parameters are presented in Table 3. A colorless prism 0.120×0.100×0.060 mm in size was mounted on a Cryoloop with Paratone oil. Data were collected in a nitrogen gas stream at 90(2) K using phi and omega scans. Crystal-to-detector distance was 40 mm and exposure time was 0.05 seconds per frame using a scan width of 0.5°. Data collection was 100.0% complete to 67.000° in θ. A total of 26838 reflections were collected covering the indices, $-11<=h<=11$, $-13<=k<=12$, $-16<=l<=15$. 2482 reflections were found to be symmetry independent, with an $R_{int}$ of 0.0309. Indexing and unit cell refinement indicated a primitive, monoclinic lattice. The space group was found to be P 21/n (No. 14). The data were integrated and scaled using CrysAlisPro 1.171.40.42a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018.

TABLE 2

| Crystal data and structure refinement for 2a | |
| --- | --- |
| Empirical formula | $C_{11}H_{16}N_3O_3P$ |
| Formula weight | 269.24 |
| Temperature | 90(2) K. |
| Wavelength | 1.54184 Å |
| Crystal system | Monoclinic |
| Space group | P 21/c |
| Unit cell dimensions | a = 10.02570(10) Å; α = 90° |
| | b = 14.0061(2) Å; β = 91.9830(10)° |
| | c = 9.30110(10) Å; γ = 90° |
| Volume | 1305.29(3) Å$^3$ |
| Z | 4 |
| Density (calculated) | 1.370 Mg/m$^3$ |
| Absorption coefficient | 1.934 mm$^{-1}$ |
| F(000) | 568 |
| Crystal size | 0.260 × 0.190 × 0.120 mm$^3$ |
| Theta range for data collection | 4.413 to 76.337°. |
| Index ranges | $-12<=h<=12$, $-17<=k<=17$, $-11<=l<=11$ |
| Reflections collected | 28327 |
| Independent reflections | 2654 [R(int) = 0.0402] |
| Completeness to theta = 67.000° | 100.0% |
| Absorption correction | Gaussian |
| Max. and min. transmission | 1.000 and 0.474 |
| Refinement method | Full-matrix least-squares on F$^2$ |
| Data/restraints/parameters | 2654/0/166 |
| Goodness-of-fit on F$^2$ | 1.082 |
| Final R indices [I > 2 sigma(I)] | R1 = 0.0294, wR2 = 0.0844 |
| R indices (all data) | R1 = 0.0300, wR2 = 0.0848 |
| Extinction coefficient | 0.0013(3) |
| Largest diff. peak and hole | 0.304 and −0.388 e.Å$^{-3}$ |

TABLE 3

Crystal data and structure refinement for 2b

| | |
|---|---|
| Empirical formula | $C_{11}H_{16}N_3O_3P$ |
| Formula weight | 269.24 |
| Temperature | 90(2) K. |
| Wavelength | 1.54184 Å |
| Crystal system | Monoclinic |
| Space group | P 21/n |
| Unit cell dimensions | a = 9.06170(10) Å; α = 90° |
| | b = 10.80990(10) Å; β = 100.3950(10)° |
| | c = 12.86720(10) Å; γ = 90° |
| Volume | 1239.73(2) Å$^3$ |
| Z | 4 |
| Density (calculated) | 1.442 Mg/m$^3$ |
| Absorption coefficient | 2.036 mm$^{-1}$ |
| F(000) | 568 |
| Crystal size | 0.120 × 0.100 × 0.060 mm$^3$ |
| Theta range for data collection | 5.382 to 75.005°. |
| Index ranges | −11 <= h <= 11, −13 <= k <= 12, −16 <= l <= 15 |
| Reflections collected | 26838 |
| Independent reflections | 2482 [R(int) = 0.0309] |
| Completeness to theta = 67.000° | 100.0% |
| Absorption correction | Gaussian |
| Max. and min. transmission | 1.000 and 0.751 |
| Refinement method | Full-matrix least-squares on F$^2$ |
| Data/restraints/parameters | 2482/0/166 |
| Goodness-of-fit on F$^2$ | 1.017 |
| Final R indices [I > 2 sigma(I)] | R1 = 0.0298, wR2 = 0.0799 |
| R indices (all data) | R1 = 0.0302, wR2 = 0.0802 |
| Extinction coefficient | 0.0011(3) |
| Largest diff. peak and hole | 0.293 and −0.390 e.Å$^{-3}$ |

Example 46: X-Ray Analysis of 6a

X-ray quality crystals were used as received. The obtained crystal parameters are presented in Table 4. A colorless blade 0.060×0.040×0.020 mm in size was mounted on a Cryoloop with Paratone oil. Data were collected in a nitrogen gas stream at 90(2) K using phi and omega scans. Crystal-to-detector distance was 40 mm and exposure time was 0.05 seconds per frame using a scan width of 0.5°. Data collection was 100.0% complete to 67.000° in θ. A total of 3584 reflections were collected covering the indices, −7<=h<=7, −9<=k<=9, −20<=l<=20. 3584 reflections were found to be symmetry independent, with an R$_{int}$ of 0.0398. Indexing and unit cell refinement indicated a primitive, triclinic lattice. The space group was found to be P-1 (No. 2). The data were integrated and scaled using CrysAlisPro 1.171.40.57a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018.

TABLE 4

Crystal data and structure refinement for 6a

| | |
|---|---|
| Empirical formula | $C_{21}H_{20}N_4$ |
| Formula weight | 328.41 |
| Temperature | 90(2) K. |
| Wavelength | 1.54184 Å |
| Crystal system | Triclinic |
| Space group | P −1 |
| Unit cell dimensions | a = 6.18230(10) Å$^3$ α = 93.764(2)° |
| | b = 7.98120(10) Å$^3$ β = 100.158(2)° |
| | c = 16.6323(5) Å$^3$ γ = 101.8850(10)° |
| Volume | 786.05(3) Å$^3$ |
| Z | 2 |
| Density (calculated) | 1.388 Mg/m$^3$ |
| Absorption coefficient | 0.660 mm$^{-1}$ |
| F(000) | 348 |
| Crystal size | 0.060 × 0.040 × 0.020 mm$^3$ |
| Theta range for data collection | 2.714 to 75.027° |
| Index ranges | −7 <= h <= 7, −9 <= k <= 9, −20 <= l <= 20 |
| Reflections collected | 3584 |
| Independent reflections | 3584 [R(int) = 0.0398] |
| Completeness to theta = 67.000° | 100.0% |
| Absorption correction | Semi-empirical from equivalents |
| Max. and min. transmission | 0.69280 and 0.67222 |
| Refinement method | Full-matrix least-squares on F$^2$ |
| Data/restraints/parameters | 3584/0/228 |
| Goodness-of-fit on F$^2$ | 1.037 |

TABLE 4-continued

Crystal data and structure refinement for 6a

| | |
|---|---|
| Final R indices [I > 2 sigma(I)] | R1 = 0.0330, wR2 = 0.0904 |
| R indices (all data) | R1 = 0.0344, wR2 = 0.0917 |
| Extinction coefficient | 0.0063(7) |
| Largest diff. peak and hole | 0.234 and −0.191 e.Å$^{-3}$ |

Example 47: X-Ray Analysis of 6b

X-ray quality crystals were used as received. The obtained crystal parameters are presented in Table 5. A yellow prism 0.120×0.100×0.100 mm in size was mounted on a Cryoloop with Paratone oil. Data were collected in a nitrogen gas stream at 90(2) K using phi and omega scans. Crystal-to-detector distance was 40 mm and exposure time was 0.05 seconds per frame using a scan width of 0.5°. Data collection was 100.0% complete to 67.000° in θ. A total of 17501 reflections were collected covering the indices, −9<=h<=9, −12<=k<=12, −14<=l<=14. 3203 reflections were found to be symmetry independent, with an R$_{int}$ of 0.0239. Indexing and unit cell refinement indicated a primitive, triclinic lattice. The space group was found to be P-1 (No. 2). The data were integrated and scaled using CrysAlisPro 1.171.40.57a. Solution by iterative methods (SHELXT-2014) produced a complete heavy-atom phasing model. All non-hydrogen atoms were refined anisotropically by full-matrix least-squares (SHELXL-2018). All hydrogen atoms were placed using a riding model. Their positions were constrained relative to their parent atom using the appropriate HFIX command in SHELXL-2018.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A method of synthesizing an amino-imidazo-pyrimidine compound of formula (XXa), the method comprising:

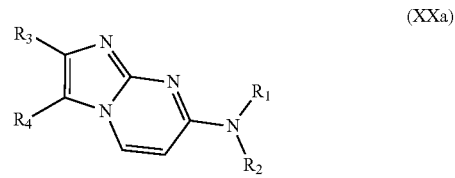

(XXa)

coupling a first compound of formula XX-P1a with a second compound of formula XX-P2

TABLE 5

Crystal data and structure refinement for 6b

| | |
|---|---|
| Empirical formula | C$_{21}$H$_{20}$N$_4$ |
| Formula weight | 328.41 |
| Temperature | 90(2) K. |
| Wavelength | 1.54184 Å |
| Crystal system | Triclinic |
| Space group | P −1 |
| Unit cell dimensions | a = 7.4777(2) Å$^3$  α = 66.420(2)° |
| | b = 10.5138(3) Å$^3$  β = 86.080(2)° |
| | c = 11.8565(3) Å$^3$  γ = 73.372(2)° |
| Volume | 817.46(4) Å$^3$ |
| Z | 2 |
| Density (calculated) | 1.334 Mg/m$^3$ |
| Absorption coefficient | 0.634 mm$^{-1}$ |
| F(000) | 348 |
| Crystal size | 0.120 × 0.100 × 0.100 mm$^3$ |
| Theta range for data collection | 4.074 to 75.450°. |
| Index ranges | −9 <= h< = 9, −12 <= k <= 12, −14 <= l <= 14 |
| Reflections collected | 17501 |
| Independent reflections | 3203 [R(int) = 0.0239] |
| Completeness to theta = 67.000 | 100.0% |
| Absorption correction | Semi-empirical from equivalents |
| Max. and min. transmission | 1.00000 and 0.85575 |
| Refinement method | Full-matrix least-squares on F$^2$ |
| Data/restraints/parameters | 3203/0/227 |
| Goodness-of-fit on F$^2$ | 1.020 |
| Final R indices [I > 2 sigma(I)] | R1 = 0.0329, wR2 = 0.0853 |
| R indices (all data) | R1 = 0.0342, wR2 = 0.0863 |
| Extinction coefficient | 0.0070(8) |
| Largest diff. peak and hole | 0.249 and −0.192 e.Å$^{-3}$ |

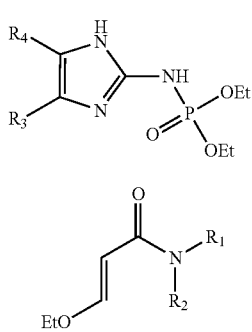 (XX-P1a)

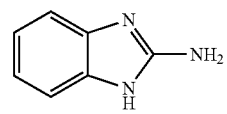 (XX-P2)

wherein:
- $R_1$ and $R_2$ are each independently selected from alkyl, alkenyl, alkynyl, carbocyclyl, aryl or heteroaryl, wherein any such group may optionally be substituted independently at one or more of its available positions by a group selected from: hydroxyl, amino, alkoxy, aminoalkyl, thio, carboxy, cyano, halo, alkyl, cycloalkyl, aryl and heteroaryl, or
- $R_1$ and $R_2$ together with the nitrogen to which they are bonded form a ring having 3-12 atoms, wherein the ring is optionally and independently substituted in any one or more of its available positions by a group selected from hydroxyl, amino, alkoxy, aminoalkyl, carboxy, cyano, thio, halo, alkyl, haloalkyl, cycloalkyl, aryl, and heteroaryl;
- $R_3$ and $R_4$ are each independently selected from alkyl, alkenyl, alkynyl, haloalkyl, carboxylate, carbocyclyl, aryl and heteroaryl, wherein any such group may optionally be substituted independently at one or more of its available positions by a group selected from: hydroxyl, amino, alkoxy, aminoalkyl, thio, cyano, halo, aryl and heteroaryl; or
- $R_3$ and $R_4$ together with the two carbon atoms of the imidazole ring to which they are respectively bonded form a phenyl ring, wherein the phenyl ring is optionally and independently substituted in any one or more of its 4 available positions by a group selected from hydroxyl, amino, alkoxy, aminoalkyl, thio, nitro, sulfonyl, carboxy, cyano, halo, alkyl, cycloalkyl, aryl, and heteroaryl, wherein any such group may optionally be substituted independently at one or more of its available positions by a group selected from: hydroxyl, amino, alkoxy, aminoalkyl, thio, nitro, haloalkyl, sulfonyl, cyano, halo, alkyl, cycloalkyl, aryl and heteroaryl; and the coupling takes place in the presence of $PCl_5$ or $POCl_3$, a base, and a non-aqueous solvent.

2. The method of claim 1, wherein the base is a tri-alkyl amine.

3. The method of claim 1, wherein $R_3$ and $R_4$ taken together with the two carbon atoms of the imidazole ring to which they are respectively bonded form a phenyl ring.

4. The method of claim 3 wherein the compound of formula (XX-P1a) is synthesized by a method comprising: reacting with $PCl(O)(OEt)_2$, N-methylimidazole, and MeCN.

5. The method of claim 4, wherein the $PCl(O)(OEt)_2$ is formed by reacting diethyl hydriogen phosphate with 1,3,5-trichloro-1,3,5-triazinane-2,4,6-trione.

6. The method of claim 1, wherein the compound of formula XX-P2 is formed as follows:
reacting (E)-3-ethoxy-acrylic acid with a chlorinating agent selected from oxalyl chloride, $SOCl_2$, and an alkyl chloroformate selected from methyl, ethyl, isopropyl and isobutyl chloroformate, to form (E)-3-ethoxyacryloyl chloride; and
reacting (E)-3-ethoxyacryloyl chloride with amine $R_1R_2NH$, in an aprotic solvent.

7. The method of claim 6, wherein the chlorinating agent is $SOCl_2$.

8. The method of claim 1, wherein the non-aqueous solvent is MeCN, MeTHF or a mixture thereof.

* * * * *